(12) United States Patent
Sochor

(10) Patent No.: US 8,543,222 B1
(45) Date of Patent: Sep. 24, 2013

(54) IMPLANTABLE LEAD AND ACCESSORIES

(76) Inventor: Jerzy Roman Sochor, Sunnyvale, CA (US)

(*) Notice: Subject to any disclaimer, the term of this patent is extended or adjusted under 35 U.S.C. 154(b) by 876 days.

(21) Appl. No.: 12/541,887

(22) Filed: Aug. 14, 2009

(51) Int. Cl.
*A61N 1/05* (2006.01)

(52) U.S. Cl.
USPC .................................................. 607/116

(58) Field of Classification Search
USPC ................................ 607/116; 604/523–532
See application file for complete search history.

(56) References Cited

U.S. PATENT DOCUMENTS

| | | | |
|---|---|---|---|
| 4,769,006 A * | 9/1988 | Papantonakos | 604/95.02 |
| 5,843,148 A | 12/1998 | Gijsbers et al. | |
| 6,413,263 B1 | 7/2002 | Lobdill et al. | |
| 6,477,427 B1 | 11/2002 | Stolz et al. | |
| 6,606,521 B2 | 8/2003 | Paspa et al. | |
| 7,033,326 B1 | 4/2006 | Pianca et al. | |
| 7,450,997 B1 | 11/2008 | Pianca et al. | |
| 7,454,251 B2 | 11/2008 | Rezai et al. | |

* cited by examiner

*Primary Examiner* — Amanda Patton

(57) ABSTRACT

An implantable stimulation lead for introduction into the brain or other anatomical target in a human body comprises a distal electrode terminal, a proximal connector terminal, and a connecting conductor cable. The led construction enables stylet means to bypass the cable and the connector terminal. A slotted cannula allows the cable and the connector terminal to be decoupled from the lead introduction tools. This enables a substantial stylet means and allows the cable and the connector terminal to be optimized without constraints of the lead introduction tools. The overall length of the lead is minimized and the conductor cable and the connector can be non-isodiametric. A method of terminating conductors to electrodes using inserts is suitable for very fine wires and stranded conductors. The disclosed leads and accessories are applicable to stimulation leads, sensing leads, or any other lead that may be implanted with or without a stereotactic localization system.

62 Claims, 24 Drawing Sheets

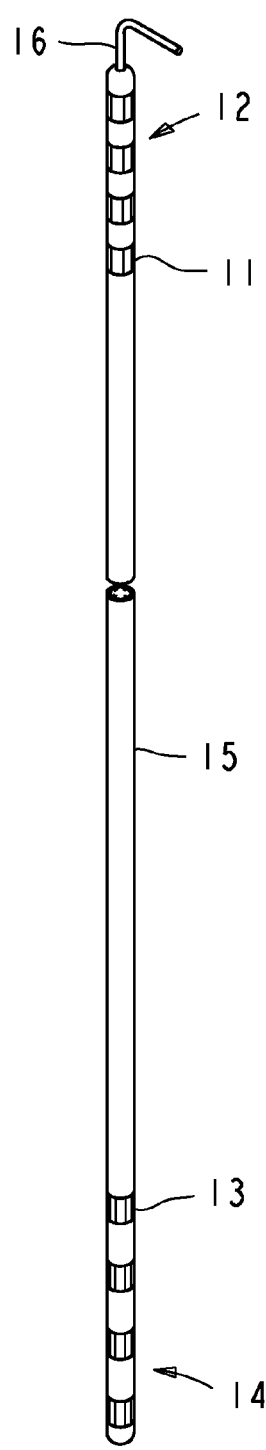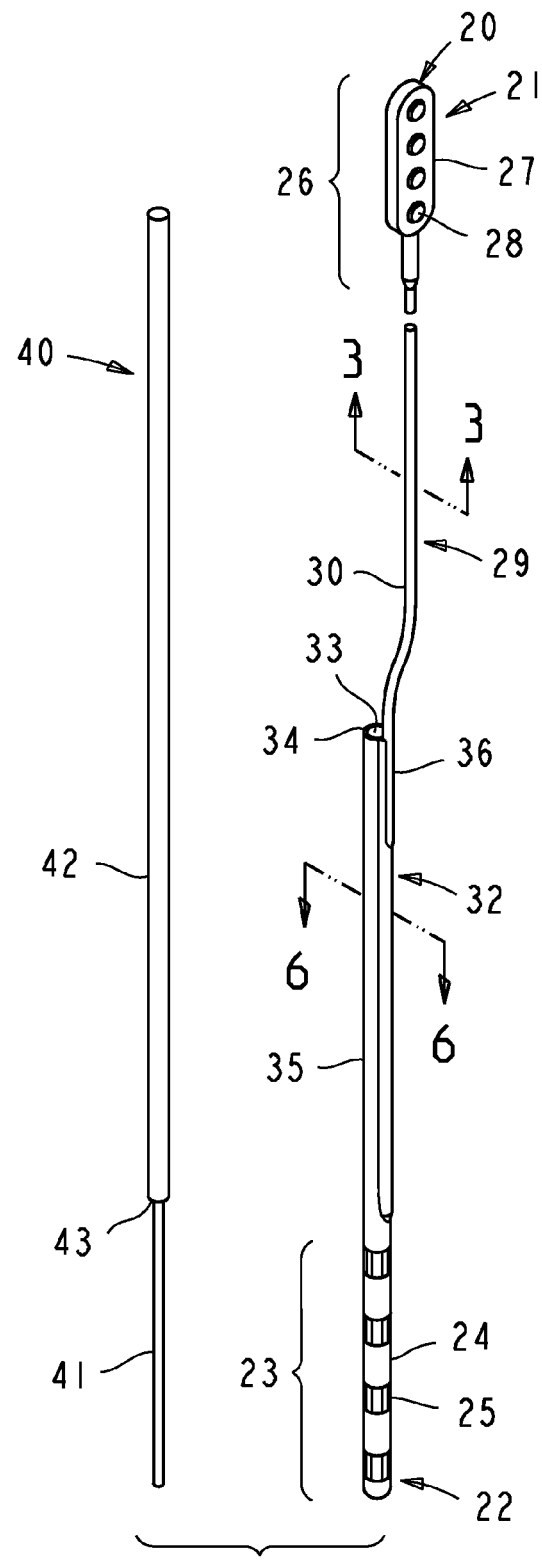
Fig. 1
(PRIOR ART)
Fig. 2

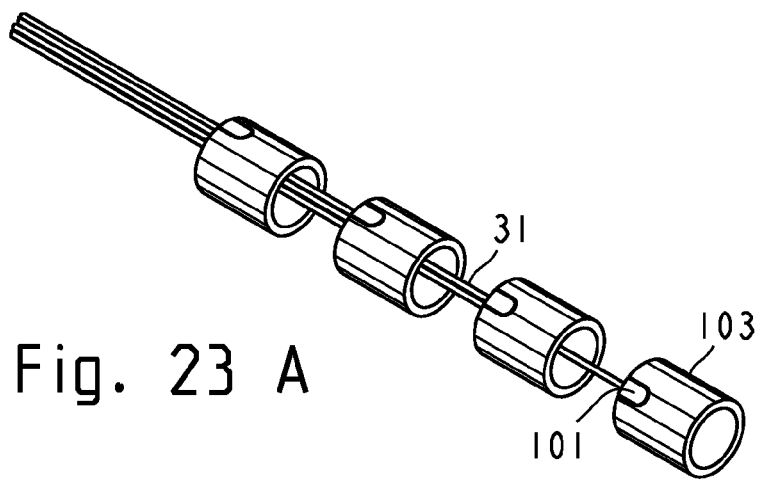
Fig. 23 A
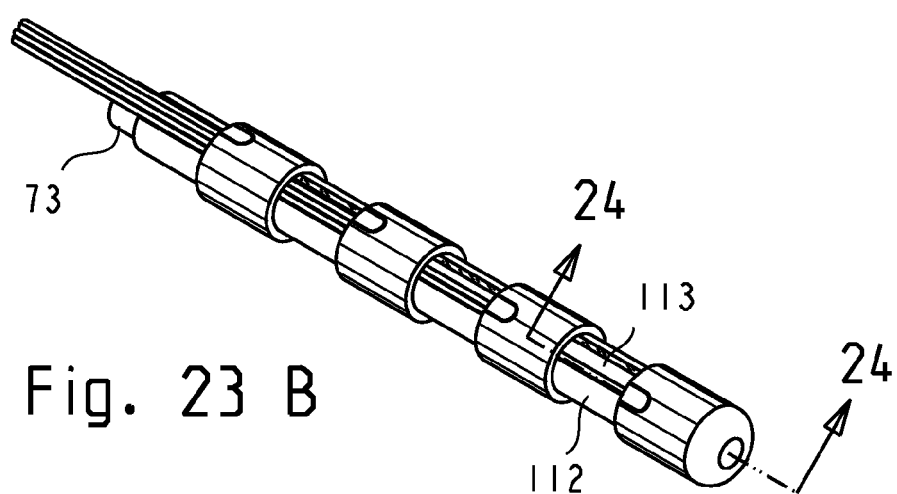
Fig. 23 B
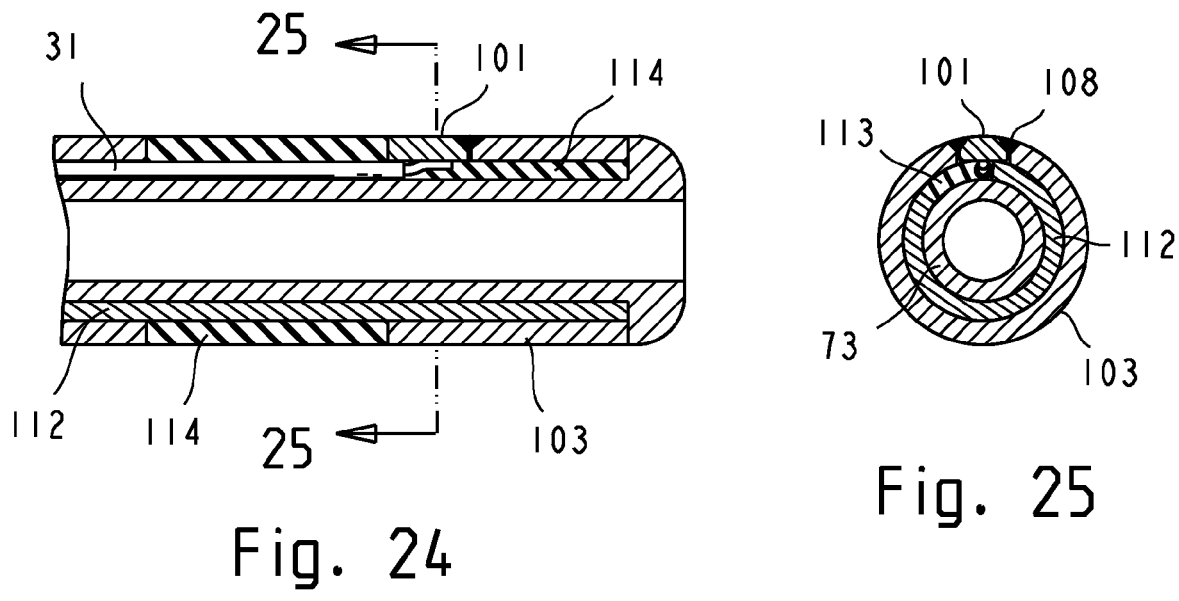
Fig. 24
Fig. 25

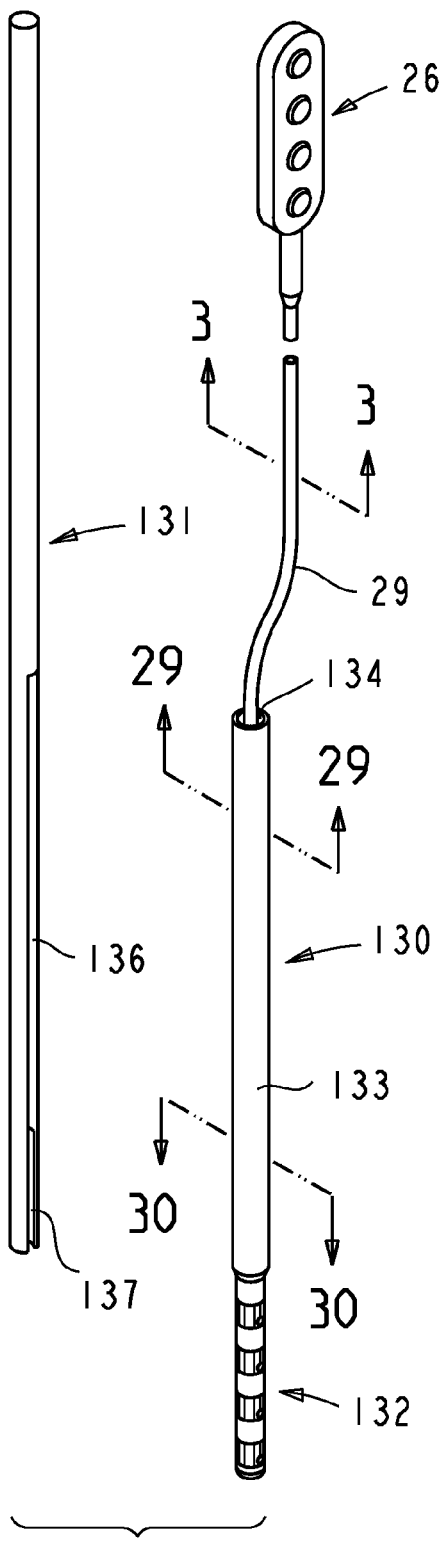
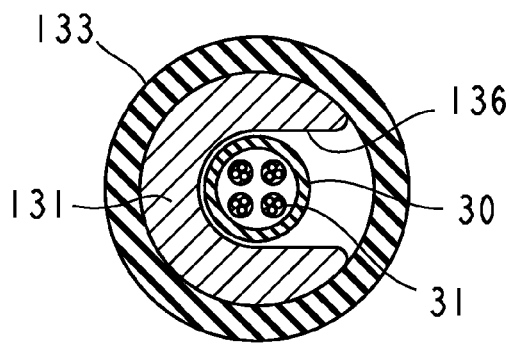
Fig. 29
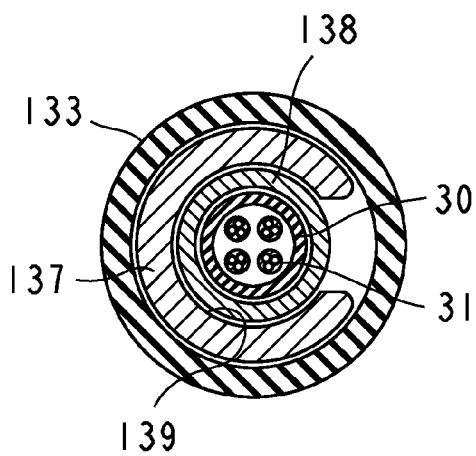
Fig. 30
Fig. 28

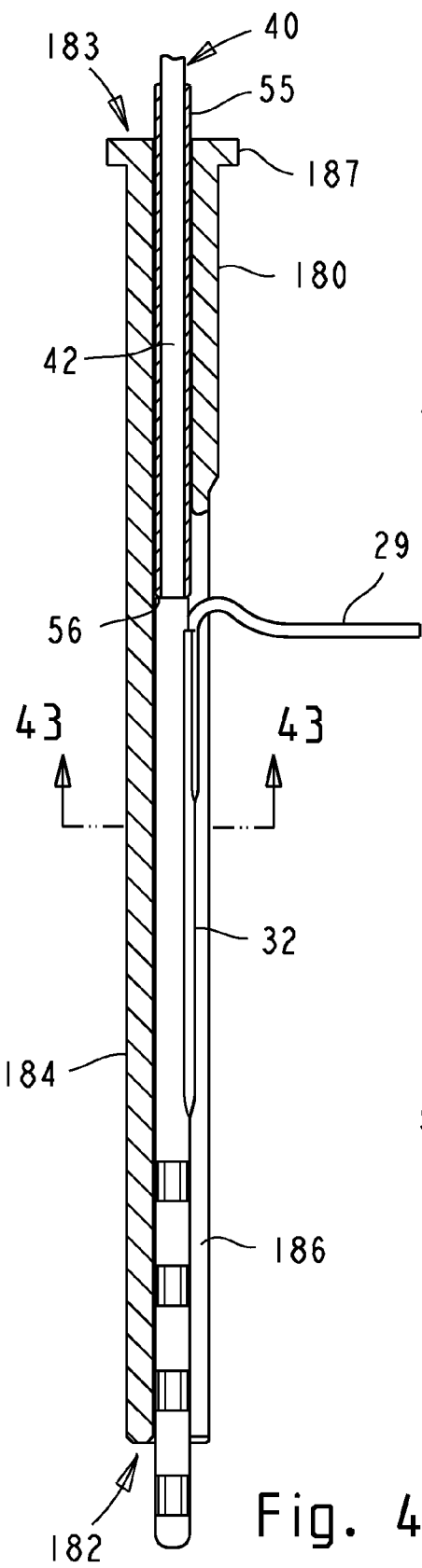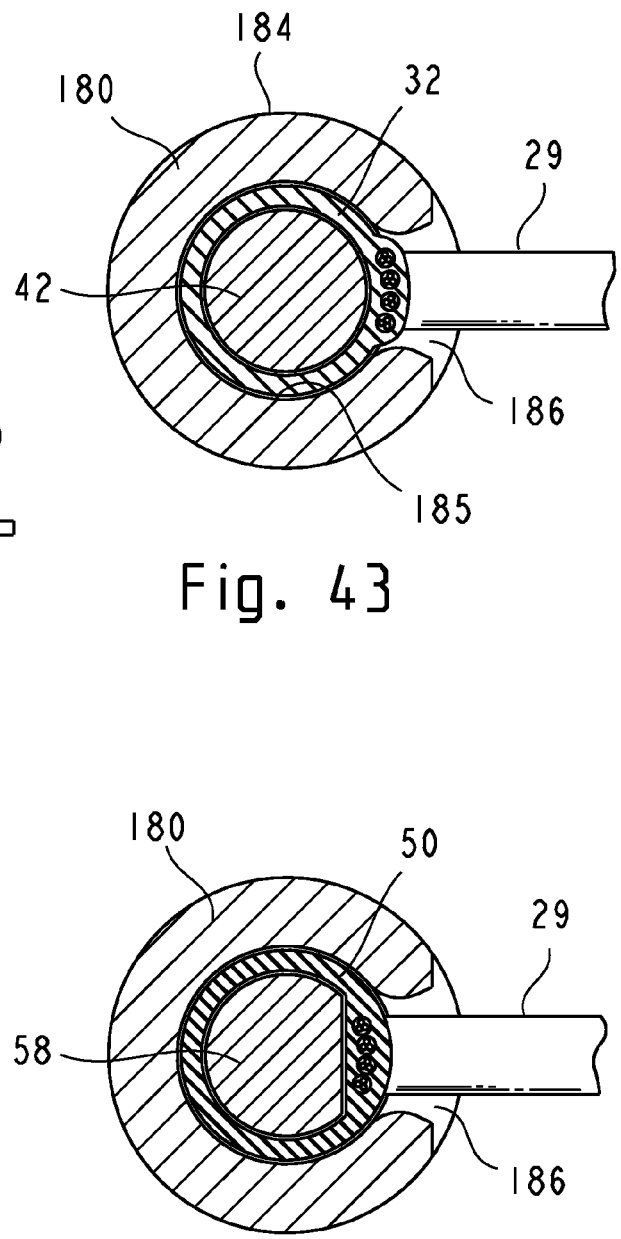
Fig. 43
Fig. 44
Fig. 42

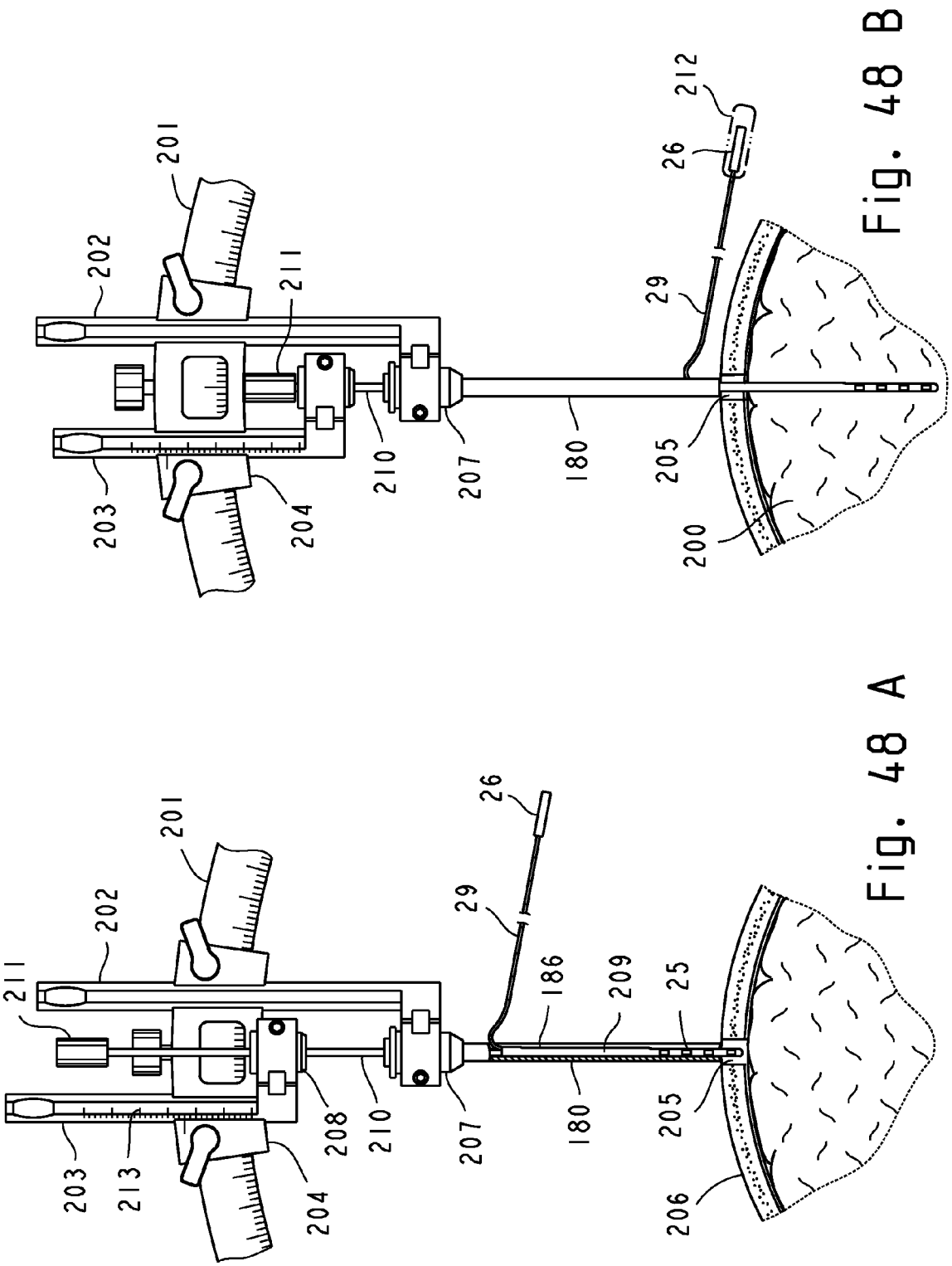

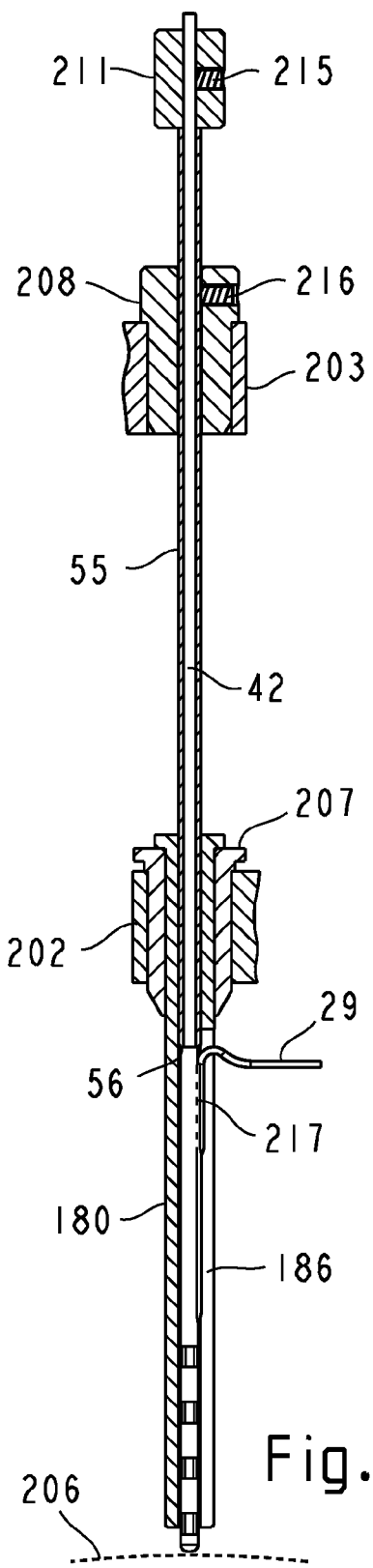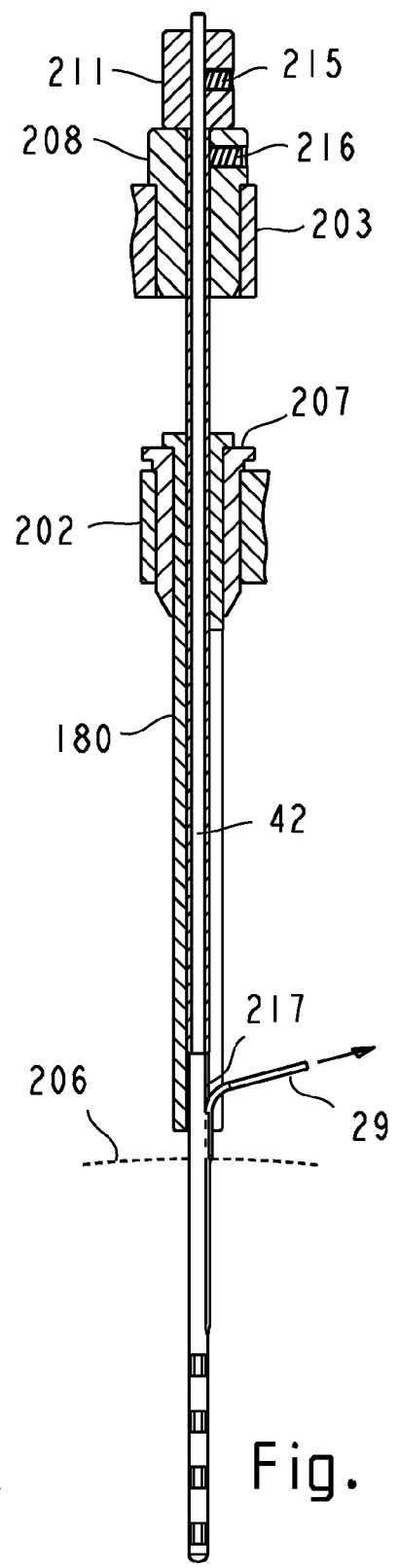

IMPLANTABLE LEAD AND ACCESSORIES

BACKGROUND

Prior Art

Electrical stimulation of neural tissue is an important therapy for treatment of movement disorders and has been proposed for numerous other conditions, such as chronic pain and epilepsy. Implantable neurostimulators find increasing use and require miniature electrical leads to transmit electrical stimuli in order to modulate and/or sense brain activity.

A typical implantable Deep Brain Stimulation (DBS) lead, shown in FIG. 1 (prior art), has contacts 11 on its proximal end 12 for connecting to an implantable device or an external test equipment and has sensing and/or stimulating electrodes 13 on its distal end 14. The electrodes are implanted in the tissue targeted for therapy (particular area of brain, spinal cord, etc.). The proximal contacts are typically connected to the respective distal electrodes by coiled conductors encased in a flexible tubular insulation 15.

The distal electrodes must be precisely implanted within the target tissue in order to achieve a desired therapeutic effect. The lead is introduced into the target tissue through a cannula (tube) and utilizes a stylet 16 to aid in passing the lead through the cannula and to provide the required flexural stiffness when the lead emerges from the cannula. The stylet is pre-installed in the lumen defined by the central opening of the conductor coil (not shown). The entire lead is usually iso-diametric since it must pass through the cannula.

A stereotactic frame (a rigid structure having markers defining a three-dimensional coordinate system) and a semicircular arc (stereotactic arc) are typically used to facilitate implantation of a DBS lead within the target tissue. The frame is firmly attached to the patient's head and a calibration imaging, such as Magnetic Resonance Imaging (MRI) is performed to determine the spatial coordinates of the target tissue relative to the frame. Once this anatomical mapping is completed the stereotactic arc with appropriate instrumentation is rigidly attached to the frame. The system is based on the center-of-arc principle wherein the center of the stereotactic arc coincides with the selected anatomical target in the brain. The use of such frame in combination with intra-operative physiological mapping of the target site and/or test stimulation enables a very precise localization (preferably within 1.0 mm) of the lead electrodes in the anatomical target in the brain.

Current practices for implanting sensing and/or stimulating DBS leads are described in U.S. Pat. No. 7,450,997 to Pianca et al (Nov. 11, 2008) and can be summarized in the following exemplary outline:

(1) Pre-operative preparation and planning. A stereotactic frame is firmly affixed to the patient's head and a standard imaging technique, such as magnetic resonance imaging (MRI), is used to identify the anatomical structure which is the target for therapy. Using radio-opaque markers in the frame as references, the spatial coordinates of the target relative to the frame are determined.

(2) Entry site preparation. A stereotactic arc with appropriate coordinate setting is attached to the stereotactic frame and the location for a lead entry into the brain (insertion trajectory) is selected. The arc is removed and a burr hole is created in the skull. A small opening in the dura (hard covering) is made and a burr hole ring is placed in the burr hole. The stereotactic arc is instrumented with appropriate cannula guide and lead stop and re-attached to the frame.

(3) Localization and verification of stimulation target. A cannula is advanced through the guide tube into the brain, to a point approximately 25 mm above the anticipated target site. A test electrode (or a DBS lead) is introduced through the cannula until the distal electrode emerges from the cannula. Test stimulation is applied and a test electrode is slowly advanced, e.g., 1 mm at a time, to identify position for optimum therapeutic response. (Several insertion trajectories may be attempted before the optimum response is achieved.) Once the optimal therapeutic effect with minimum side effects is achieved, the location of the test electrode is recorded (to be used for DBS lead placement) and the test electrode is removed (if a DBS lead is used for test stimulation, the lead is already in the desired location).

(Optionally, a recording microelectrode probe is used before or concurrently with stage (3) for high resolution (sub-1.0 mm) localization of the target. A microelectrode cannula is inserted into the brain until it is approximately 25 mm above the anticipated target site. A recording microelectrode probe is introduced through the cannula until the microelectrode emerges from the cannula. The microelectrode is gradually advanced while probing for the functional boundary of the target region. Once the optimal target region is identified, the microelectrode cannula and the microelectrode are removed.)

(4) Lead implantation and intra-operative stimulation. The lead depth stop gauge is attached on the lead to stop the lead at the point corresponding to the optimal target point determined by the test electrode. The lead is advanced slowly along the trajectory made by the test electrode. Intra-operative stimulation is performed using an external stimulator to verify the response. When the optimum stimulation mode and electrode configuration are determined and the desired response has been achieved with minimal side effects, the settings are recorded.

(5) Stylet removal and lead stabilization. The lead is securely fastened in the lead holder groove. The adjustable depth stop gauge is removed from the insertion cannula. The insertion cannula is withdrawn from brain until the lead can be seen between the burr hole and the cannula. While holding the lead at the point it exits the skull, the stylet is disengaged and removed from the lead. Still holding the lead at exit point from the skull, the insertion cannula and the guide tube assembly are removed. The stimulation effect is rechecked and lead placement verified. The lead is locked in the anchor.

(6) Device implantation. A pocket is created at the top of the skull at the edge of the burr hole incision for placement of the excess lead wire and connector. The excess lead is coiled and placed into the pocket. The device is implanted and connected to the lead.

While variations of the above outlined procedure are practiced, the following factors are common in the art:

(A) The cannula used to guide the lead into the stimulation target is inserted into the brain. Since the diameter of the cannula is significantly larger than that of the lead, the cannula displaces significantly more brain tissue than the lead alone. This increases the risk of a brain injury or hemorrhage, especially if multiple insertion trajectories and/or lead repositioning are required to achieve successful localization.

(B) The lead is introduced into the cannula from the proximal end of the cannula; the entire lead must clear the lumen in the cannula and therefore the lead is usually iso-diametric. A lead with an iso-diametric proximal end limits connector options, e.g., a paddle shaped connector is generally not feasible, unless a splittable cannula is used. (While splittable cannulas have been proposed they are not favored for DBS implantation due to impracticality in small size, possibility of brain trauma, and lead dislodgement issues.)

(C) As the cannula is removed from the brain to expose the lead at the exit from the skull, the lead's proximal end must still be attached to a lead holder (otherwise the cannula would drag the lead with it due traction on the lead). In addition, the lead's proximal contacts must be accessible for test stimulation. Only after the lead is securely held at the exit from the skull and a test stimulation verifies lead dislodgement had not occurred the lead can be detached from the lead holder and the cannula and associated lead introduction tools can be completely removed. The above constraints cause the lead to be very long, e.g., 400 mm or longer.

(D) The long lead-cannula interface generates significant traction on the lead when the cannula is being withdrawn, which contributes to a lead dislodgement. When an inadvertent lead dislodgement occurs, a repositioning of the lead may be necessary, increasing the risk and expense of the procedure. A long lead also creates lead management problem since a significant lead volume must be accommodated under the scalp. Crossing lead sections can lead to lead wire shorts under prolonged pressure.

Similarly, a variety of stimulation leads are in use but they typically have these features:

(A) A typical lead is iso-diametric throughout its length with an outside diameter of approximately 1.3 mm.

(B) Coiled conductors are prevalent. The coiled conductors naturally provide a stylet lumen and assure a flexible lead. However the coiled conductors are difficult to terminate to the lead electrodes and contacts and increase the complexity of lead construction. While coiled conductors impart flexibility, the leads with coiled conductors have a relatively poor crush resistance and are susceptible to kinking if the minimum bend radius, e.g., at the exit from a connector or from a lead anchor, is not observed. In addition the coiled wire is very fine and a robust joint to an electrode or a contact is difficult to achieve.

(C) The lead has a factory pre-installed stylet which should not be re-inserted into the lead intra-operatively once it is removed. (The coiled wire has a very thin insulation which can be easily damaged in the attempt to re-insert the stylet into the coil lumen.) If a repositioning of the lead is required after the stylet is removed, a use of new lead is mandated.

A critical factor affecting reliability and manufacturability of the presently used leads is the termination of conductors to respective electrodes and contacts. Various termination techniques have been proposed for coiled and non-coiled conductors to make these terminations more robust and easier to manufacture.

U.S. Pat. No. 6,185,463 to Baudino (Feb. 6, 2001) discloses a method for non-coiled conductors wherein an electrically conductive C-shaped ring electrode is introduced onto the notched section on the lead by moving the notched section into the open part of the electrode. The electrode is subsequently formed into a cylindrical shape by closing it so that its opposing edges are brought to an abutting relationship. A single conductor is brought through the insulation and aligned with a hole on the electrode to be welded to the electrode, for example, by laser welding. The final affixation procedure involves welding the abutting surfaces of the electrodes together, thereby securely forming a ring electrode recessed within the notch on the lead.

U.S. Pat. No. 6,477,427 to Stolz et al (Nov. 5, 2002) discloses a method for terminating coiled conductors to electrodes wherein the lead has a contact sleeve with a through radial hole for receipt of the wire member and describes method of manufacture. A coil member is used that has a fixed pitch portion and a variable pitch portion, extending at least one filar (a protruding end of wire) member radially from the coil member, placing a lead body over the coil member, providing a contact sleeve over a portion of the lead body, the contact sleeve having a slot for receipt of the filar member, and welding the filar member to the contact sleeve.

U.S. Pat. No. 5,843,148 to Gijsbers et al (Dec. 9, 1998) discloses a brain stimulation lead for precise delivery of electrical stimuli to a small dense brain target, and method of positioning such lead optimally in the patient's brain. The lead has a plurality of electrodes characterized by a diagonal geometry, permitting a greater number of electrodes to be provided within a very small lineal distance, e.g. 10 mm or even 5 mm. However, the transition of coiled conductors to the electrodes is not shown and conductor-to-electrode connection is only shown diagrammatically. The patent further suggests that the use of a highly rigid stylet provides the possibility of performing stereotactic placement without the need of any additional aid such as a cannula. However the main body of the lead appears to be conventional construction with a multi-conductor coil, lumen within the coil in which is placed a stylet, and a diameter typically of about 0.13 cm.

Small anatomical brain targets such as the subthalamic nucleus require lead localization with a high spatial resolution and implantation procedure that minimizes micro-dislodgment of the electrodes when the lead insertion tools are being removed and when the lead is being anchored at the burr hole. Even a sub-millimeter dislodgement of the lead may result in a loss of therapy or undesirable side effects.

U.S. Pat. No. 6,413,263 to Lobdill et al (Jul. 2, 2002) addresses the problem of an excessive length of the lead (referred to as a probe) by disclosing "a stereotactic probe holder for maintaining a probe in position, where the stereotactic probe holder contacts the probe at a position between a stereotactic frame and a patient's head, and where the stereotactic probe holder comprises an adjustable support, a locking means effective to substantially immobilize the stereotactic probe holder, and a gripping means, attached to the adjustable support, that is effective to hold the probe."

However, the device can immobilize the lead only after the brain cannula is retracted to expose the lead, which retraction may in itself be a cause of lead dislodgement. In addition, the probe holder is yet another tool to be attached to a stereotactic system which increases setup complexity and may undesirably obscure access to the burr hole site.

Therefore, lead systems and lead introduction methods to eliminate or minimize dislodgement of the DBS are desirable, preferably using the native introduction tools, i.e., without additional devices attachable to the stereotactic frame. Removal of the lead introduction tools without manual intervention (manually holding the lead) is also desired.

One advantage of coiled conductors is their flexibility and resistance to a flexing fatigue. This is especially critical if the lead is placed in an articulated part of the body and/or is passing through a mobile tissue, e.g., passing through the neck. While brain tissue and under-the-scalp environment are essentially immobile, coiled wire conductors are nonetheless common in DBS leads due to their flexibility and amenability to receiving a stylet in the coil's lumen. Another important requirement for a DBS lead is the crush resistance, since the lead may be routed over skull irregularities, and may be inadvertently crossing itself. However, the crush resistance is rather poor in the leads utilizing coiled conductors.

The process of arriving at the final and efficacious lead position in the target may involve multiple incremental steps, employing recording of cell activities and test stimulation. If lead localization is not successful, it may be necessary to adjust the stereotactic coordinates and attempt a different trajectory. If a lead localization is successful but a lead dislodgement occurs (e.g., due to removal of introduction tools) it may be necessary to repeat introduction of the lead along the same trajectory. Robust leads and introduction tools are therefore needed that could withstand multiple introduction cycles.

Present leads cannot be fully optimized due to limitations of traditional iso-diametric construction based on coiled conductors, and the interdependence of this construction and introduction tools. For example, entire lead must accommodate a stylet and be passable through an insertion cannula. This makes the lead excessively long, which is essentially dictated by the lead introduction method rather than by functional interconnection requirements. Similarly, the iso-diametric proximal connector terminal, typically having ring contacts similar to the electrodes, limits device connector options.

U.S. Pat. No. 7,454,251 to Rezai et al (Nov. 18, 2008) lists numerous issues caused by an excessive lead length (susceptibility to electromagnetic radiation or "antenna effect", MRI safety, random management of excess lead, difficulty in making revision surgery, etc.) and discloses a device and method for retaining an excess portion of a lead implanted within or on surface of a brain of a patient.

SUMMARY

In one or more aspects the present implantable medical leads and systems address the need for improved leads for use with implantable devices, such as a neurostimulator. One lead construction is disclosed which allows a distal electrode terminal, a proximal connector terminal, and a connecting cable to be optimized independently. This has multiple advantages:
(a) Only a brain-implantable portion of the lead receives the stylet and engages the introduction tools. The remaining portions of the lead are decoupled from the stylet and lead introduction tools.
(b) The cable connecting distal electrodes to proximal contacts can be short, since it is decoupled from the stylet and the introduction tools. The length of the lead is not dictated by the introduction tools. This allows the lead to have a desirably short length.
(c) The proximal connector can have a paddle configuration or any other desirable configuration since it does not need to be passable through a cannula.
(d) A variety of conductor and cable constructions can be used to provide flexibility and high crush resistance.
(e) A robust lead construction and a short stylet engagement length allow the stylet to be re-inserted into the lead once removed.

A method of terminating conductors to electrodes using inserts is suitable for very fine wires and particularly advantageous for stranded conductors. Multiple insert configurations are disclosed.

Multiple embodiments of a reinforced electrode terminal can be coupled with a stylet in a manner that reduces flexing of the distal end of the lead. The reinforcing also facilitates robust small-dimensioned electrode terminals which are resistant to flexing and buckling and are therefore suitable for repeated lead introductions.

In still another aspect, tools and methods for a precise introduction of a lead into the target tissue are adapted for use with a microelectrode for identifying functional boundaries of the stimulation site. Improved means for introducing a microelectrode probe are provided.

In another aspect, lead introduction tools based on a slotted cannula are disclosed. A synergy between the disclosed leads and the introduction tools results in multiple advantages:
(a) The use of a brain-entering cannula is eliminated; a relatively stiff stylet provides the requisite stiffness and thus allows the cannula to remain completely out of the brain.
(b) The cable and proximal connector do not interfere with the lead introduction tools; the slotted cannula enables the cable and proximal connector to bypass the lead introduction tools,
(c) The lead introduction tools can be disassembled and removed with minimal manual handling of the lead; at least one tool constrains the lead when the other tools are removed.
(d) Lead retraction due to disassembly and removal of the lead introduction tools is minimized; a stylet sleeve holds the lead from retracting when the cannula or stylet is removed.
(e) The proximal connector is intra-operatively accessible throughout the entire procedure and need not be disconnected for the removal of the introduction tools.
(f) Short lead-stylet interface and short overall length of the introduction tools; the stylet's length is not dictated by the overall length of the lead.
(g) Compatibility with standard stereotactic instrumentation.

The method of removal of the insertion tools minimizes lead dislodgement due to manual handling of the lead. This is enabled by a stylet means comprising a stylet and a stylet sleeve. The stylet can be removed from the sheath while the stylet sleeve holds the outer end of the sheath from retracting. The stylet sleeve makes it possible to disengage the stylet from the sheath and allows a removal of the stylet and cannula without manually holding the lead from retracting. Once the stylet and cannula are removed the stylet sleeve can be lifted with the remaining insertion tools without generating traction on the lead.

DRAWINGS

FIG. 1 is a perspective view of an iso-diametric lead of the prior art, with a stylet installed.

FIG. 2 is a perspective view of an embodiment of a lead having a cable entering the sheath wall tangentially, shown side-by-side with a stylet.

Figure 14:
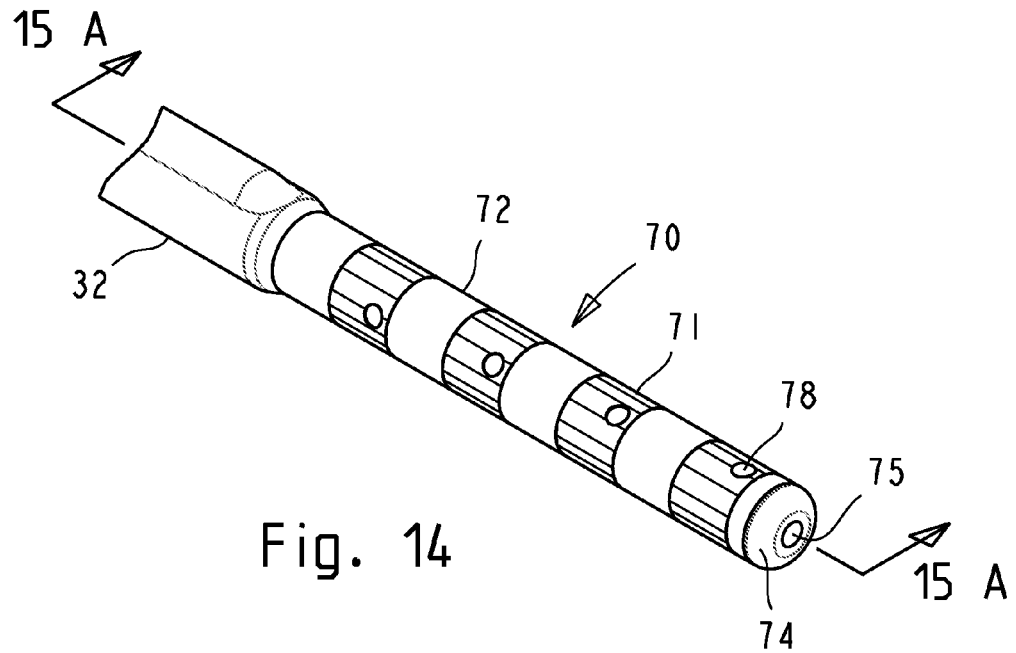
FIG. 14 is a partial perspective view of a distal end of a lead similar to that of FIG. 2, but having a higher resolution electrode terminal.
Figure 15:
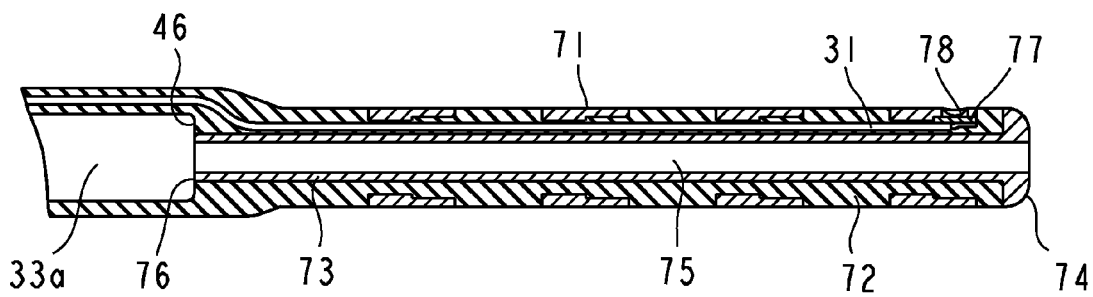
FIG. 15A is a cross-sectional view of the lead of FIG. 14, taken along the lead's longitudinal axis, as indicated by the lines 15A-15A of FIG. 14.
FIG. 15B is a cross-sectional view of the lead of FIG. 14 with added stylet, taken along the lead's longitudinal axis, as indicated by the lines 15A-15A of FIG. 14.
Figure 15:
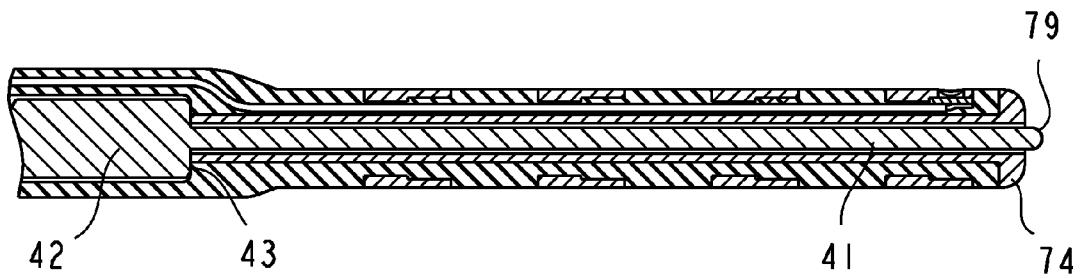
Figure 16:
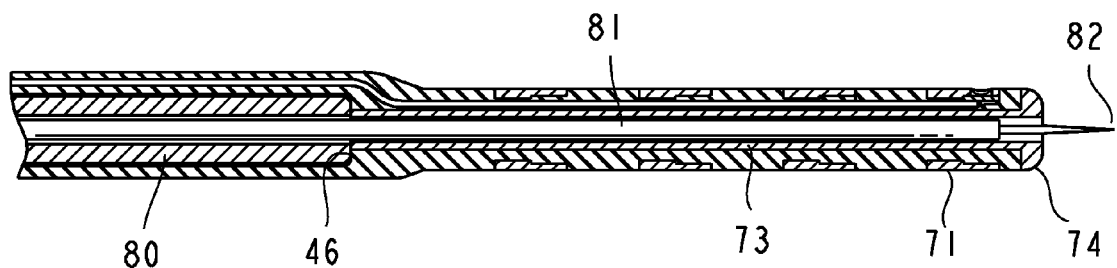
Figure 16:
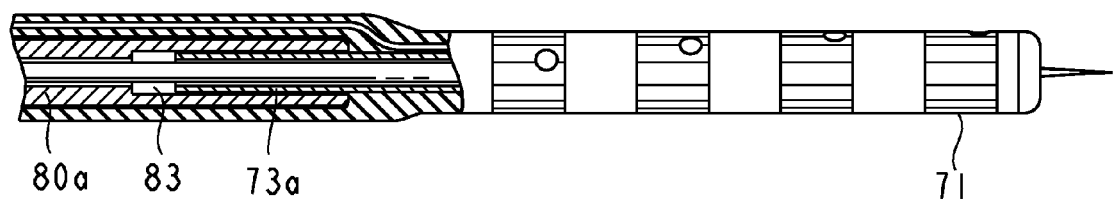
Figure 16:
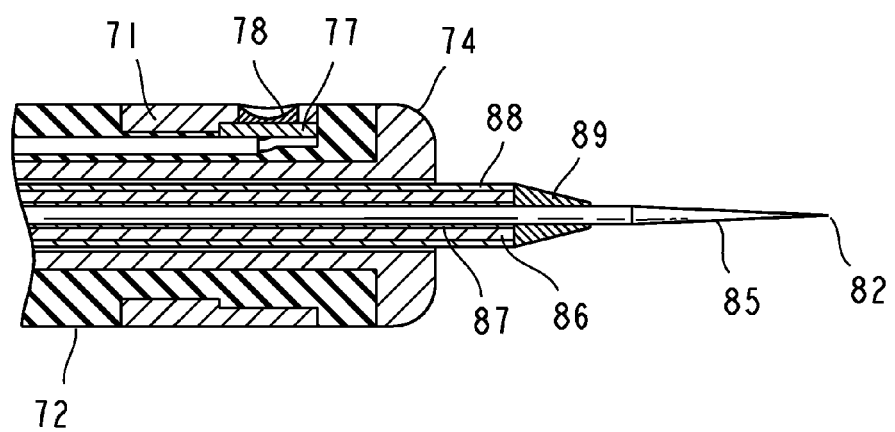

FIGS. 16A-C are partial cross-sectional views of the lead of FIG. 14, with a stylet system adapted for use with a microelectrode probe.

Figure 17:
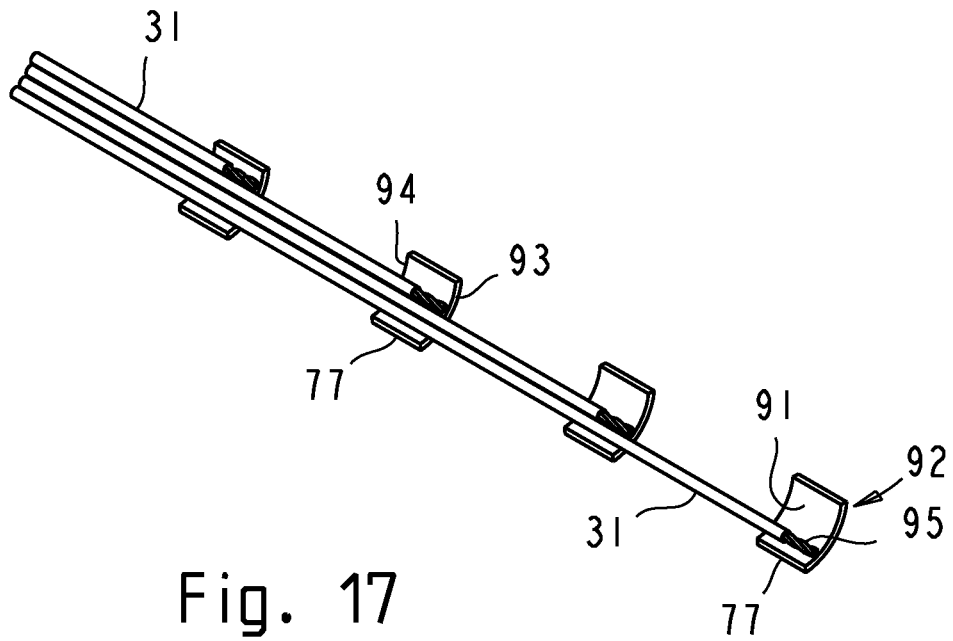

FIG. 17 is a perspective view of a conductor-insert assembly utilizing arcuate inserts.

Figure 18:
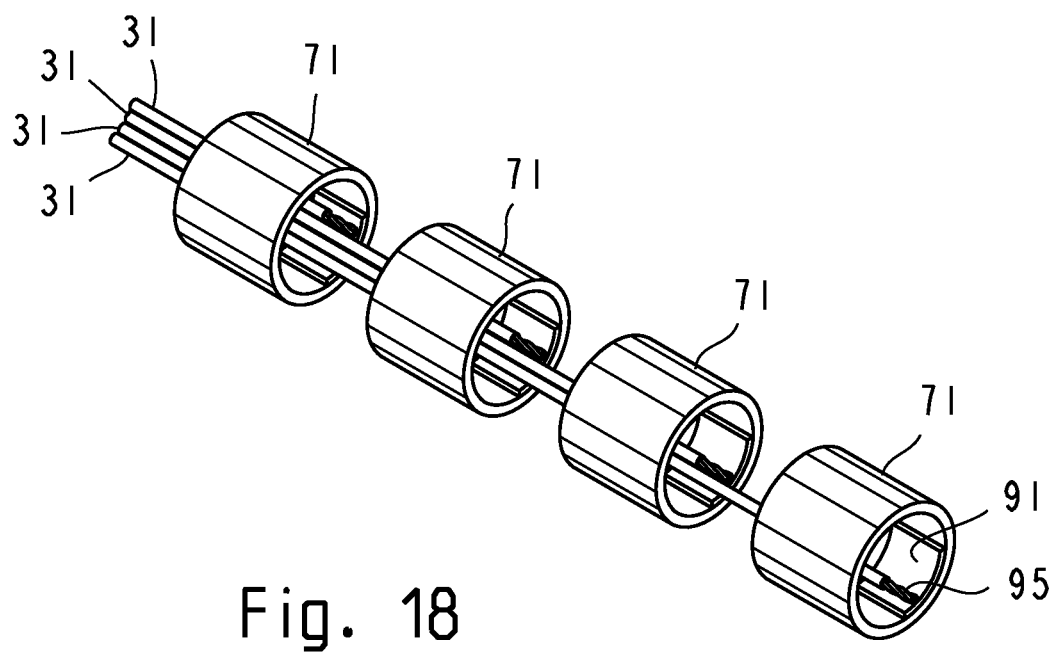

FIG. 18 is a perspective view of the conductor-insert assembly of FIG. 17 with electrodes attached.

FIGS. 19A and 19B are magnified detail views of an embodiment of a conductor-insert-electrode assembly utilizing an arcuate insert.

Figure 20:
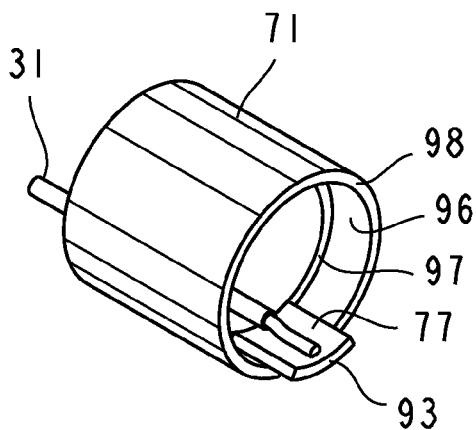
Figure 20:
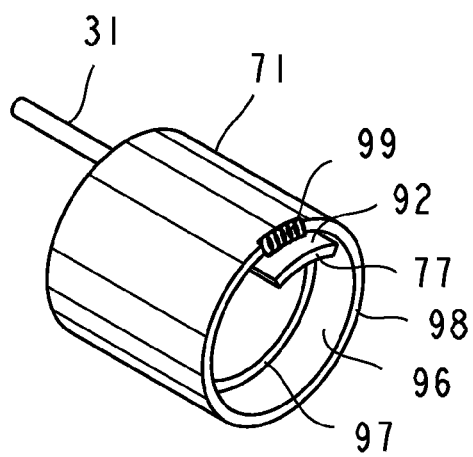

FIGS. 20A and 20B are magnified detail views of another embodiment of a conductor-insert-electrode assembly utilizing an arcuate insert.

Figure 21:
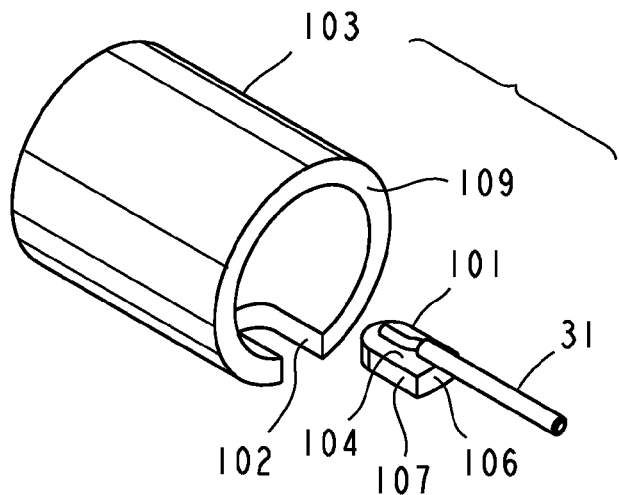
Figure 21:
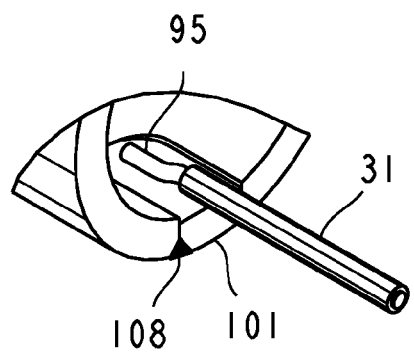
Figure 21:
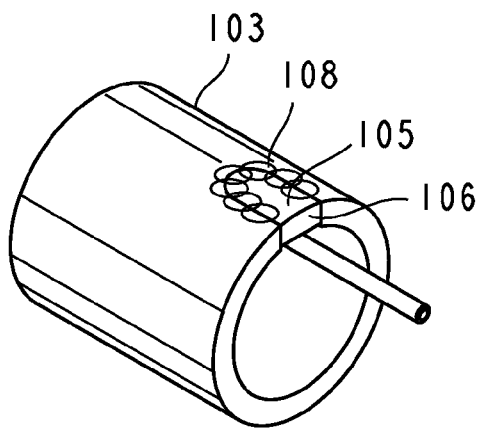

FIGS. 21A-C are detail views of an embodiment of a conductor-insert-electrode assembly utilizing inserts that are coplanar with the outer surface of the electrode after attachment.

Figure 22:
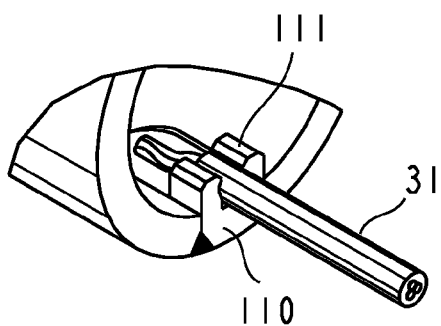

FIG. 22 is a detail view of a variation of the conductor-insert-electrode assembly of FIG. 21B.

FIG. 23A is a perspective view of an electrode terminal harness, utilizing the conductor-insert-electrode assembly of FIGS. 21A-C.

FIG. 23B is as perspective view of a partially assembled electrode terminal utilizing the electrode terminal harness of FIG. 23A.

FIG. 24 is a partial cross-sectional view of an electrode terminal after adding body insulation, taken axially as indicated by the lines 24-24 of FIG. 23B.

FIG. 25 is a cross-sectional view of the lead assembly of FIG. 24, taken at the insert, as indicated by the lines 25-25 of FIG. 24.

FIG. 26A is a perspective view of a conductor-electrode assembly with a semi-circular half-electrode.

FIG. 26B is a perspective view of a conductor-electrode assembly of FIG. 26A with a complimentary semi-circular half-electrode attached to form a ring electrode.

FIG. 27A is a perspective view of a conductor-electrode assembly with partially formed electrodes.

FIG. 27B is a perspective view of conductor-electrode assembly of FIG. 27A after forming the electrodes to a ring shape and welding the butting edges.

FIG. 28 is a perspective view of an embodiment of a lead having a high resolution electrode terminal and a cable that is exiting the sheath from within the sheath opening, shown side-by-side with a stylet.

FIG. 29 is a cross-sectional view of the lead-stylet assembly of FIG. 28, taken near the outer end of the sheath where the stylet is retentively engaged with the sheath, as indicated by the lines 29-29 of FIG. 28.

FIG. 30 is a cross-sectional view of the lead-stylet assembly of FIG. 28, taken at the portion of the sheath where the stylet is slidably engaged with the sheath, as indicated by the lines 30-30 of FIG. 28.

Figure 31:
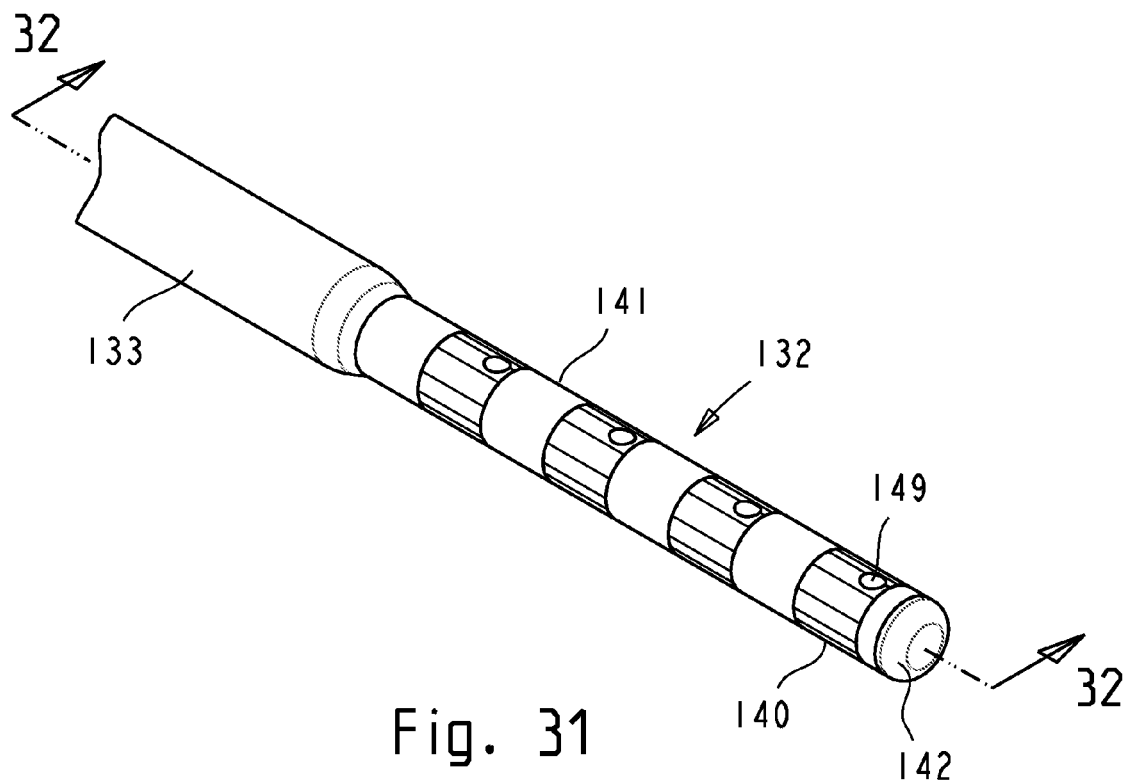

FIG. 31 is a partial perspective view of the distal portion of the lead of FIG. 28.

Figure 32:
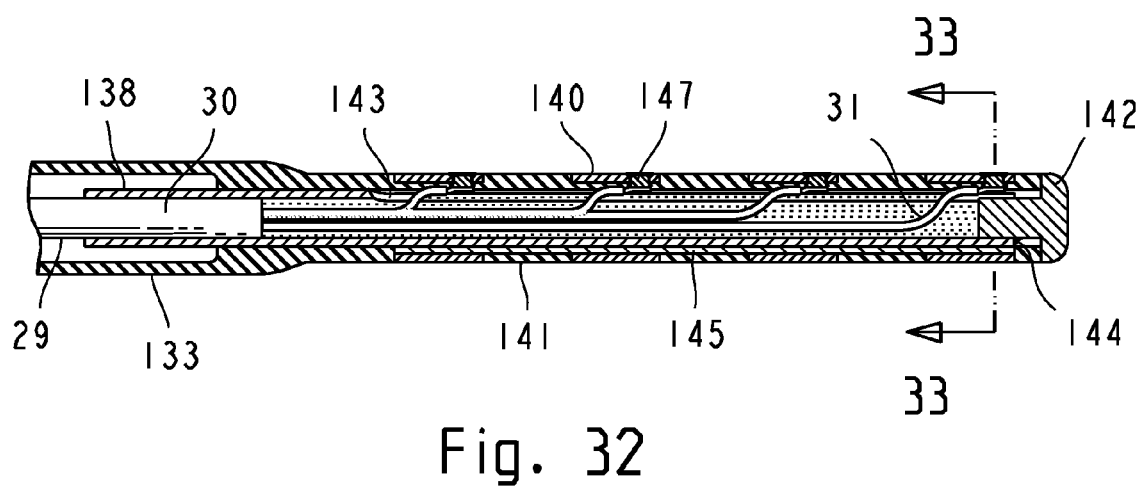

FIG. 32 is a longitudinal cross-sectional view of the lead portion of FIG. 31, taken axially, as indicated by the lines 32-32 of FIG. 31.

Figure 33:
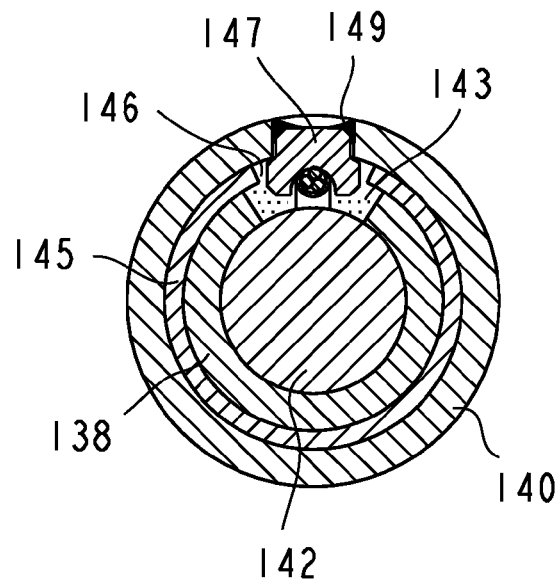

FIG. 33 is a magnified cross-sectional view of the lead portion of FIG. 32, taken as indicated by the lines 33-33 of FIG. 32.

FIGS. 34A and 34B are detail views of a conductor terminated to the insert of FIG. 33.

Figure 34:
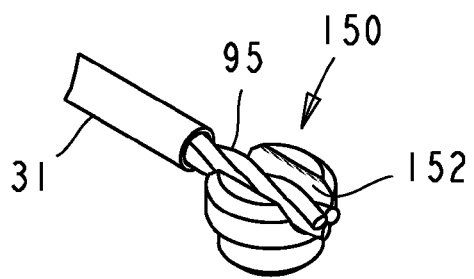
Figure 34:
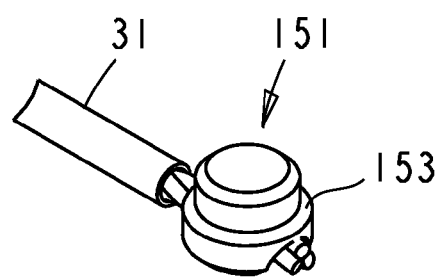
Figure 35:
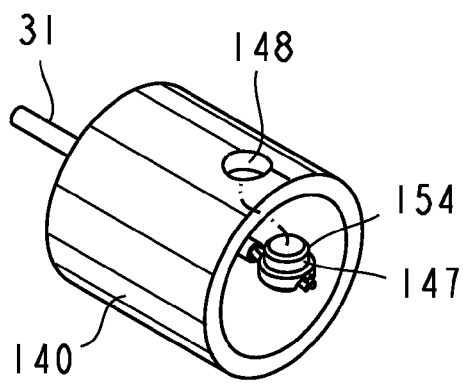

FIG. 35 is a perspective view of conductor-insert assembly of FIGS. 34A-B, shown with an electrode.

Figure 36:
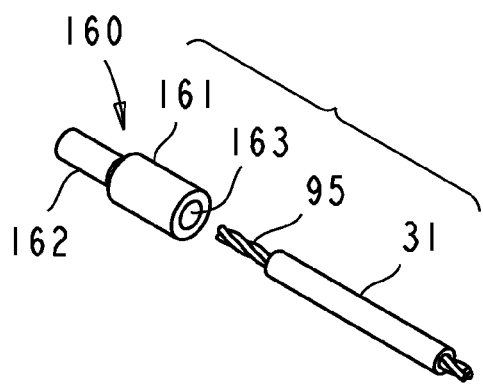

FIG. 36 shows an embodiment of a tubular insert and a conductor end portion before termination.

Figure 37:
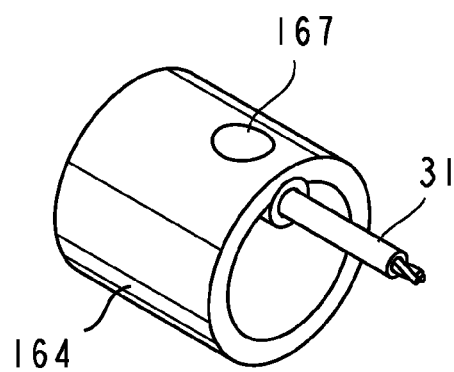

FIG. 37 shows a terminated insert-conductor pair of FIG. 36, attached to an electrode.

Figure 38:
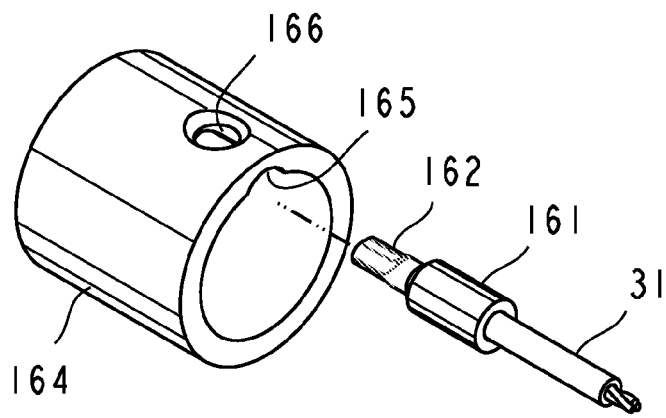

FIG. 38 shows a crimped insert-conductor pair being assembled with an electrode.

Figure 39:
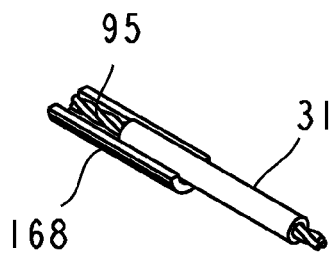

FIG. 39 shows a half-tubular insert with a corresponding conductor portion.

Figure 40:
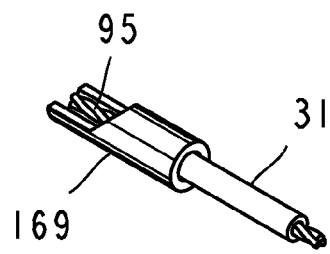

FIG. 40 shows another variation of a tubular insert with corresponding conductor portion.

Figure 41:
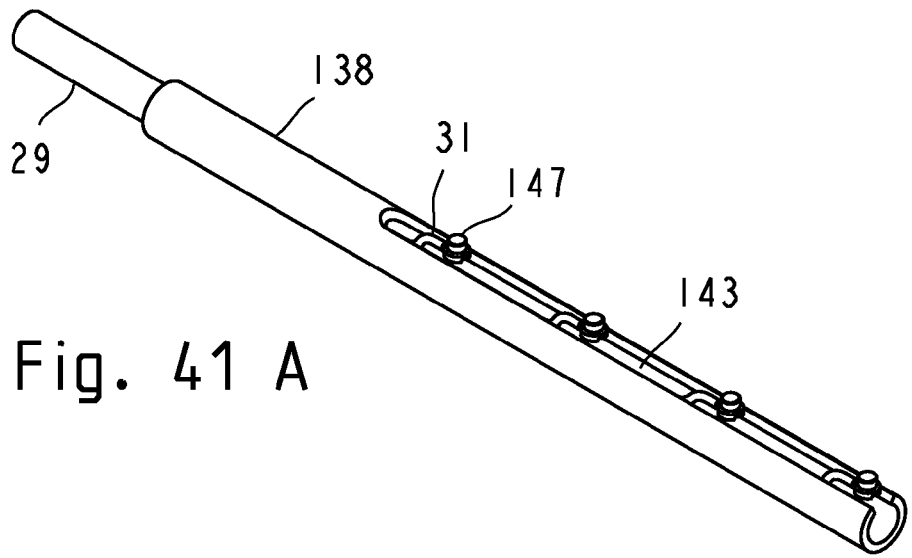
Figure 41:
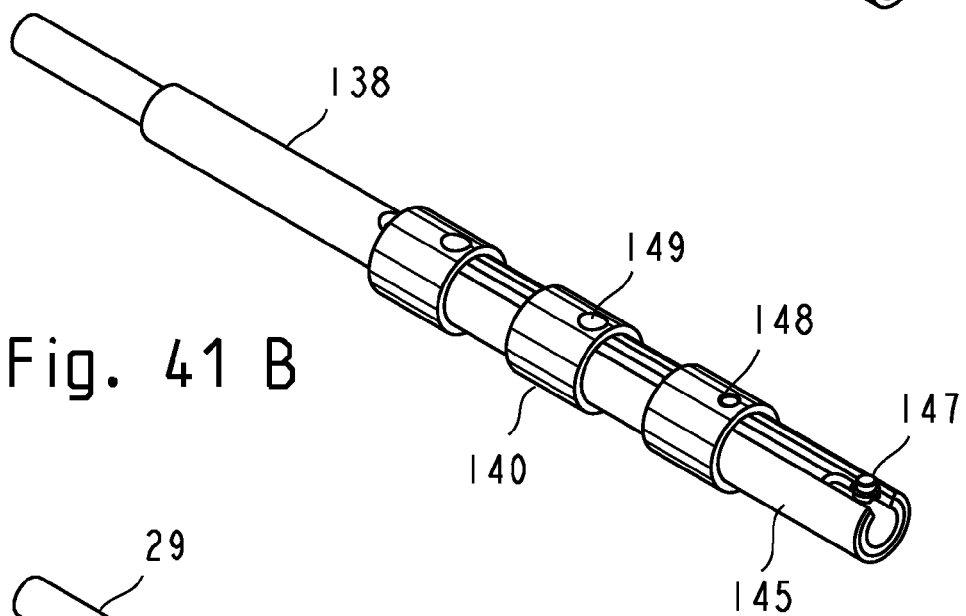
Figure 41:
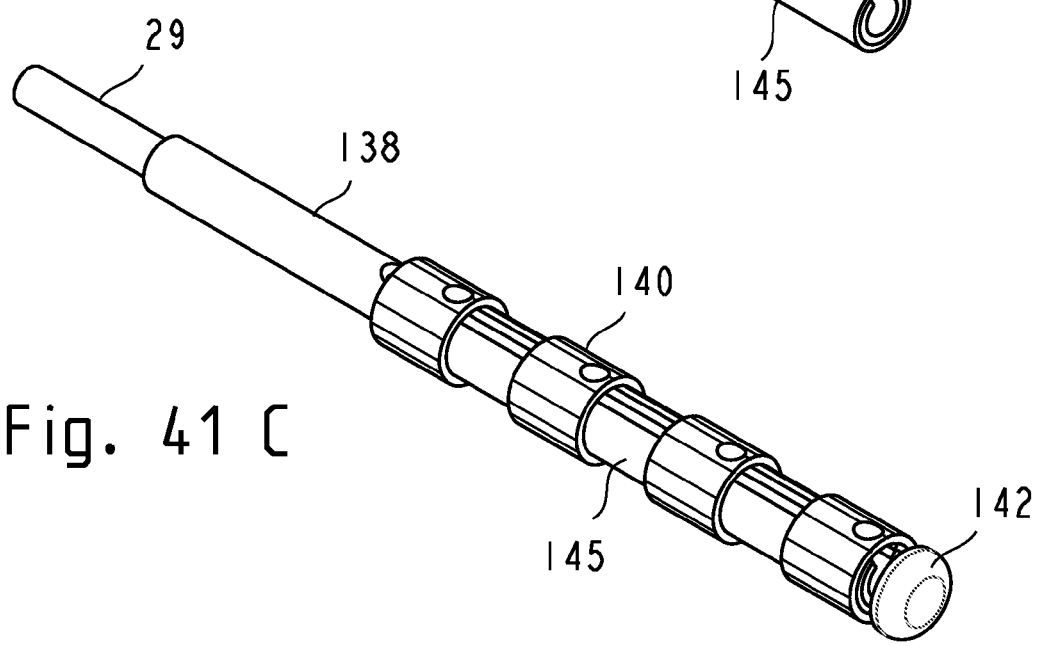

FIG. 41A-C show stages of assembly for the electrode terminal of FIG. 31.

Figure 8:
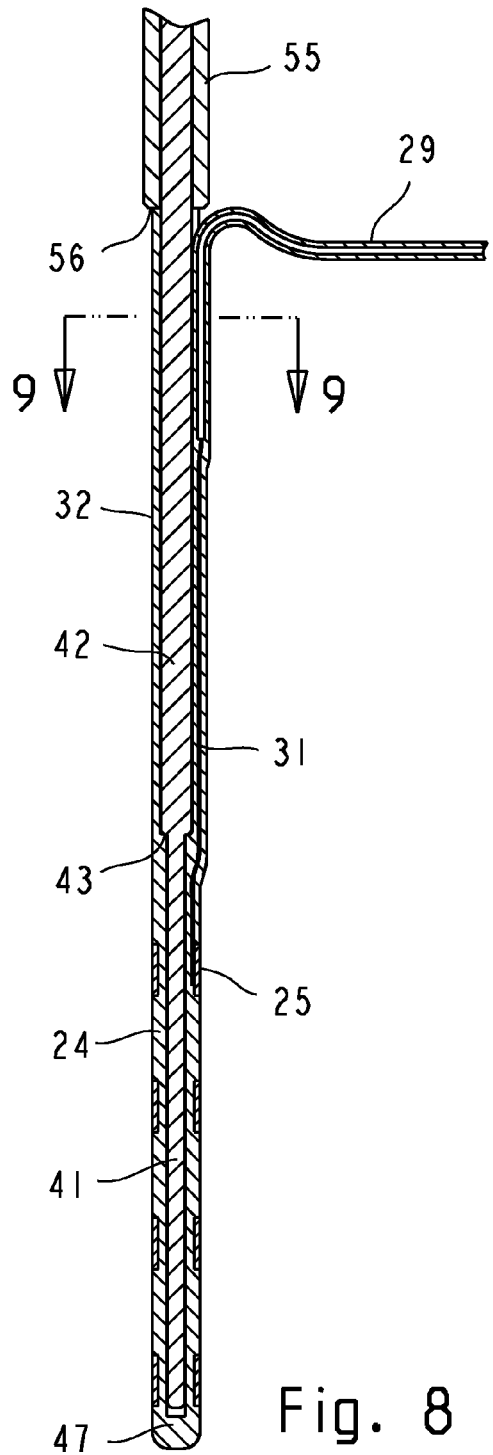
FIG. 8 is a partial cross-sectional view of the lead and stylet of FIG. 2 with the stylet inserted into the sheath, the view taken longitudinally along the lead's axis.

FIG. 42 is a cross-sectional axial view of the lead-stylet-sleeve assembly of FIG. 8 after insertion into a slotted cannula.

FIG. 43 is a cross-sectional view of the assembly of FIG. 42, taken as indicated by the lines 43-43 of FIG. 42.

FIG. 44 is a cross-sectional view equivalent to that in FIG. 43, showing a variation of lead and stylet cross-sectional profiles.

Figure 45:
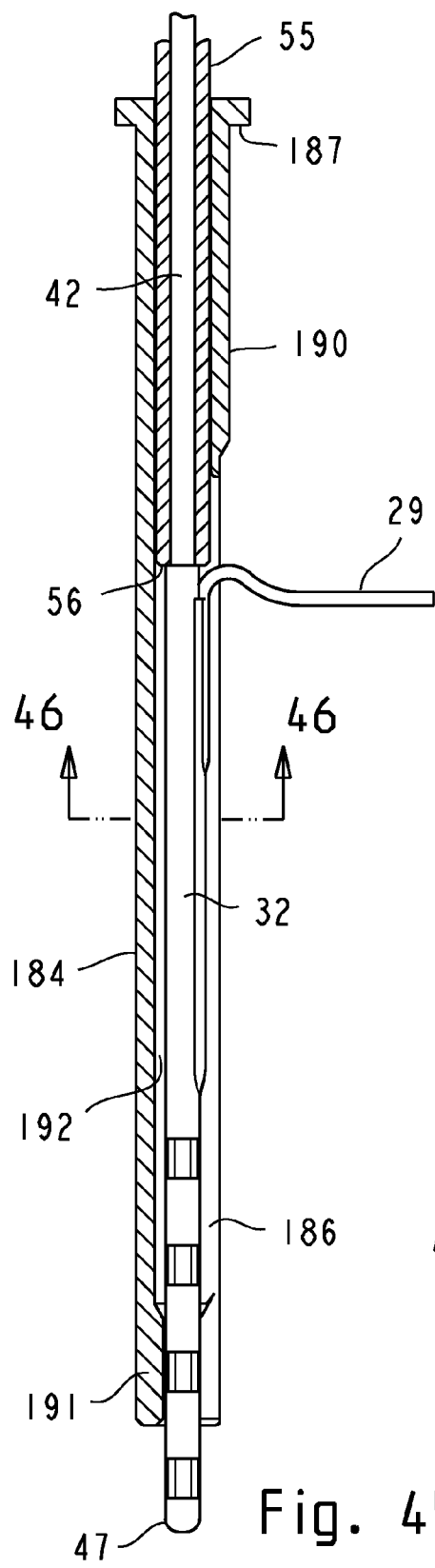

FIG. 45 shows a lead-stylet-sleeve assembly of FIG. 8, inserted into a slotted cannula with a stepped lumen.

Figure 46:
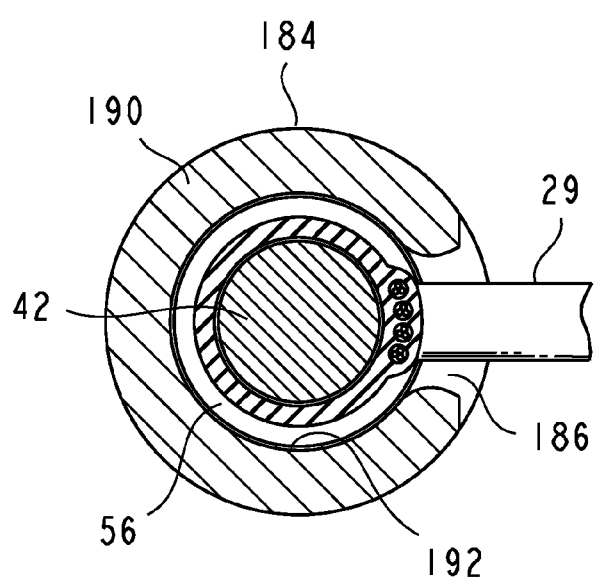

FIG. 46 is a cross-sectional view of the assembly of FIG. 45, taken as indicated by the lines 46-46 of FIG. 45.

Figure 47:
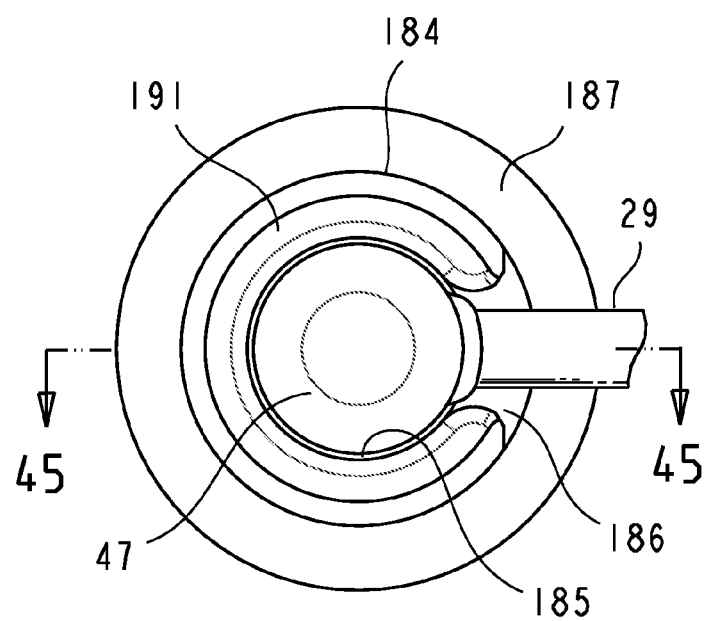

FIG. 47 is a bottom (distal end) view of the assembly of FIG. 45.

FIGS. 48A and 48B show a lead and lead introduction system utilizing a slotted cannula.

FIGS. 49A and 49B are partial magnified views of FIGS. 48A and 48B showing lead introduction tools in greater detail.

Figure 50:
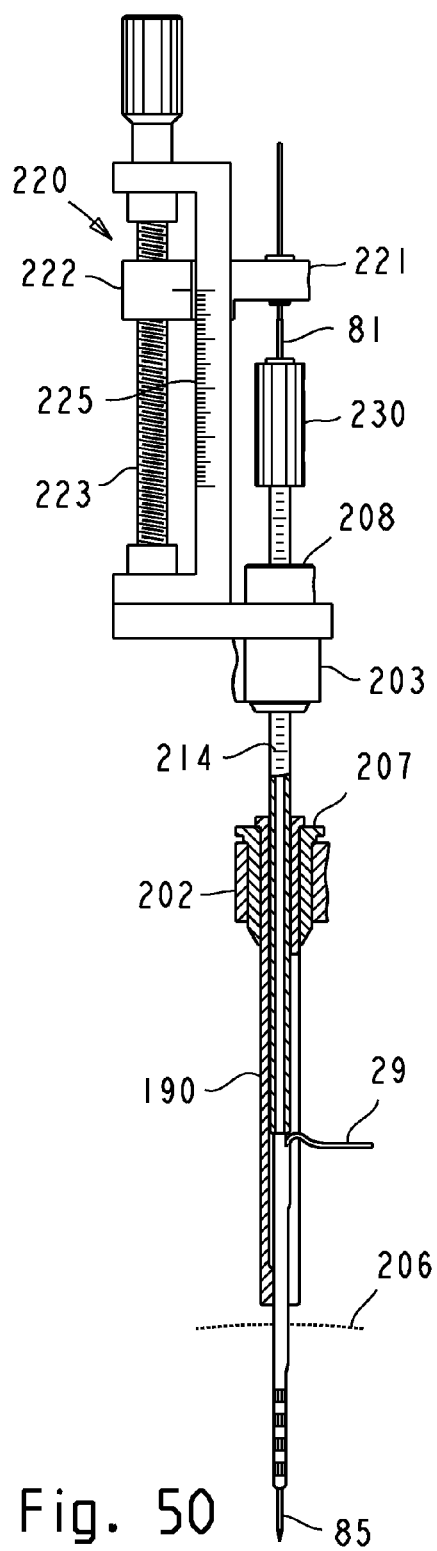
Figure 51:
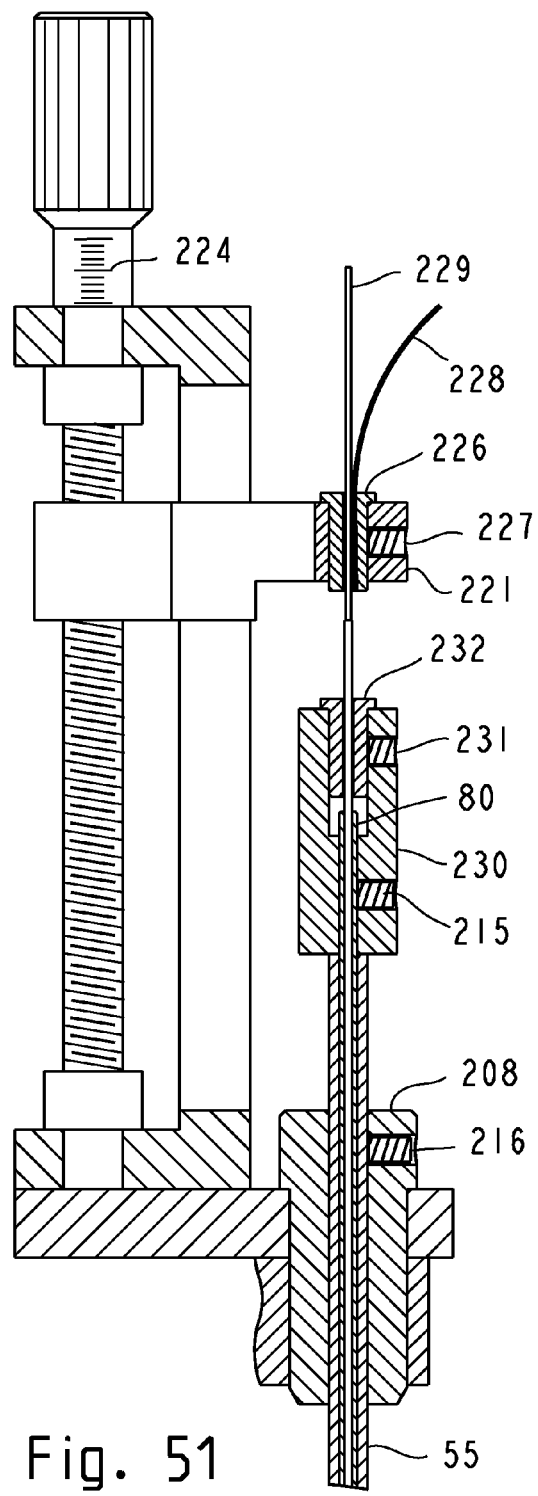

FIGS. 50 and 51 show lead introduction tools adapted for use of a microelectrode.

Figure 52:
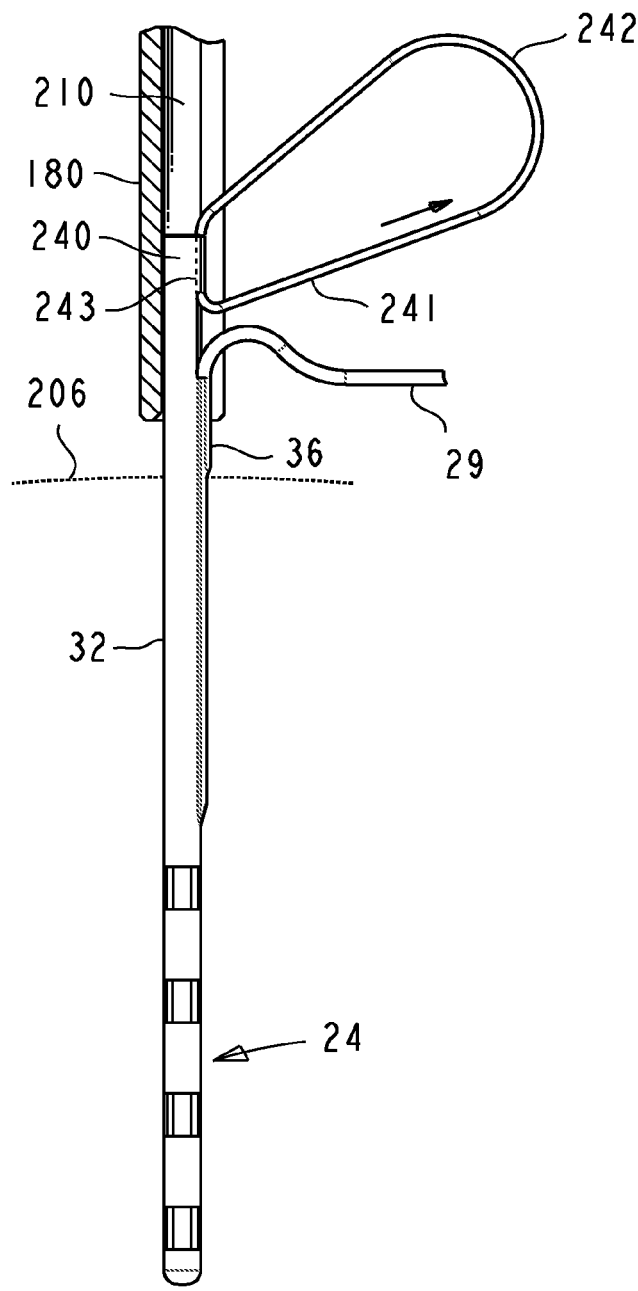
Figure 53:
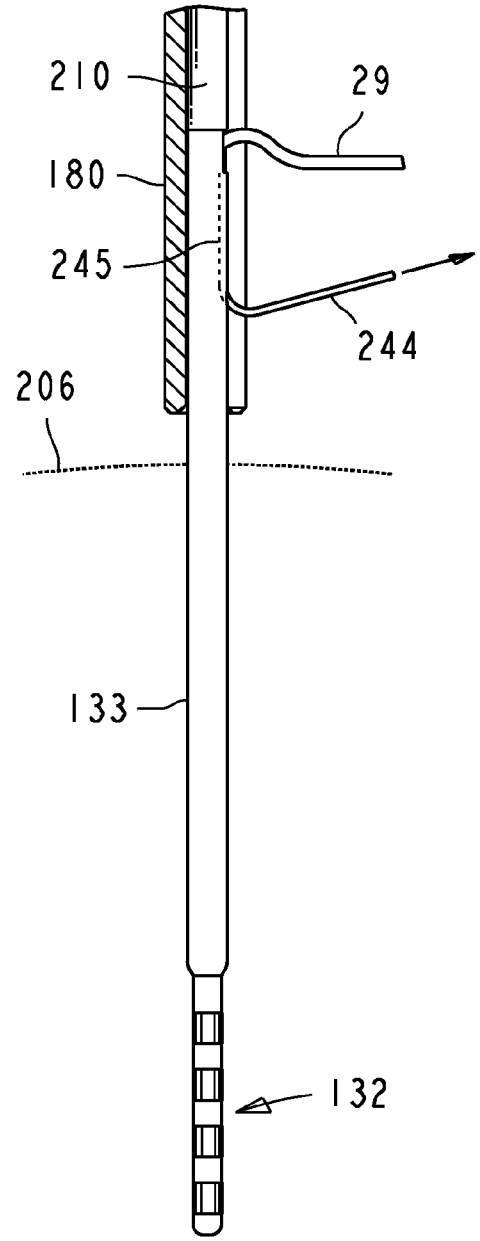

FIGS. 52 and 53 show a method of releasing a sheath from a stylet using a cutting thread.

Figure 54:
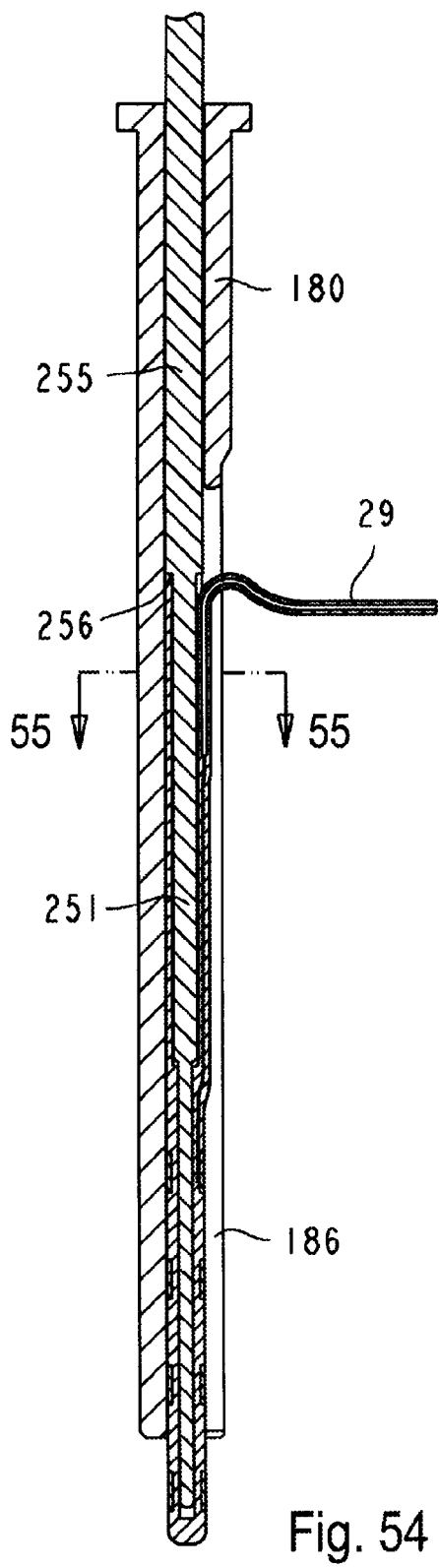
Figure 55:
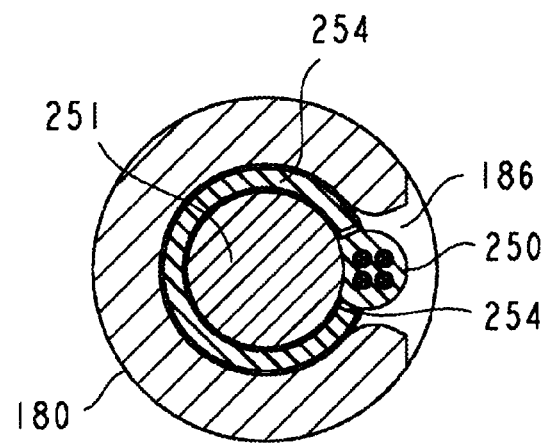

FIGS. 54-55 are a longitudinal and a cross-sectional view respectively, showing an embodiment of a lead with a cable-to-stylet retention mechanism and a peelable cable portion.

Figure 56:
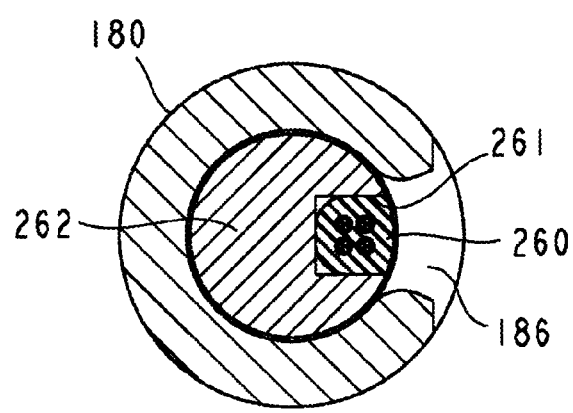

FIG. 56 is a cross-sectional view showing a variation of cable-to-lead retention mechanism.

DRAWINGS

Reference Numerals

| | |
|---|---|
| 11 | contact (prior art) |
| 12 | proximal end (prior art) |

| | | |
|---|---|---|
| 13 | electrode (prior art) | |
| 14 | distal end (prior art) | |
| 15 | insulation (prior art) | |
| 16 | stylet (prior art) | |
| 20 | lead | |
| 21 | proximal end | |
| 22 | distal end | |
| 23 | electrode terminal | |
| 24 | body, electrode terminal | |
| 25 | electrode | |
| 26 | connector terminal | |
| 27 | body, connector terminal | |
| 28 | contact | |
| 29 | cable | |
| 30 | body, insulating | |
| 31 | conductor | |
| 32 | sheath | |
| 33 | opening, sheath | |
| 34 | outer end, sheath | |
| 35 | outside surface, wall | |
| 36 | merging of cable and sheath | |
| 40 | stylet | |
| 41 | distal portion, stylet | |
| 42 | body portion, stylet | |
| 43 | step, stylet | |
| 44 | body, insulating | |
| 45 | lumen, electrode terminal | |
| 46 | bottom, sheath opening | |
| 47 | tip, distal | |
| 48 | wall, locally thickened | |
| 50 | sheath, D-shaped | |
| 51 | opening, sheath, D-shaped | |
| 52 | sheath wall thickened | |
| 55 | sleeve, stylet | |
| 56 | end, sleeve | |
| 58 | body, stylet | |
| 60 | cable, wavy | |
| 61 | casing, wavy cable | |
| 62 | body, wavy cable | |
| 63 | seal, casing-to-lead | |
| 64 | sleeve, connector body | |
| 65 | seal, casing-to-connector | |
| 66 | cable, flat | |
| 67 | insulation, flat cable | |
| 68 | core, elastomeric | |
| 69 | sleeve, cable | |
| 70 | electrode terminal, high resolution | |
| 71 | electrode | |
| 72 | body, electrode terminal | |
| 73 | tube, reinforcing | |
| 74 | tip, distal | |
| 75 | lumen | |
| 76 | proximal end, reinforcing tube | |
| 77 | insert | |
| 78 | cross hole, weld | |
| 79 | distal tip, stylet | |
| 80 | stylet, tubular | |
| 81 | microelectrode probe | |
| 82 | tip, microelectrode | |
| 83 | counterbore, stylet | |
| 85 | core, microelectrode | |
| 86 | tube, stainless, microelectrode | |
| 87 | tube, insulating, microelectrode | |
| 88 | tube, outer, microelectrode | |
| 89 | glue | |
| 91 | inner surface, insert | |
| 92 | outer surface, insert | |
| 93 | front edge, insert | |
| 94 | back edge, insert | |
| 95 | bared end, conductor | |
| 96 | recessed surface, electrode | |
| 97 | step, electrode | |
| 98 | rim, electrode | |
| 99 | weld line | |
| 101 | insert | |
| 102 | cutout, electrode | |
| 103 | electrode | |
| 104 | inner surface, insert | |
| 105 | outer surface, insert | |
| 106 | back edge, insert | |
| 107 | edge, insert | |
| 108 | weld line | |
| 109 | rim edge, electrode | |
| 110 | insert, slotted | |
| 111 | slotted portion, insert | |
| 112 | interliner tube, slit | |
| 113 | opening, slit | |
| 114 | body insulation | |
| 115 | electrode | |
| 116a | first half-electrode | |
| 116b | second half-electrode | |
| 117 | inner surface, electrode | |
| 118 | longitudinal edge, electrode | |
| 119 | weld line | |
| 120 | electrode, partially formed | |
| 121 | inner surface, electrode | |
| 122 | edge, seam | |
| 123 | weld line | |
| 124 | electrode | |
| 130 | lead, high resolution | |
| 131 | stylet | |
| 132 | electrode terminal, high resolution | |
| 133 | sheath | |
| 134 | sheath opening | |
| 136 | slot, stylet | |
| 137 | arcuate portion | |
| 138 | tube, stiffening | |
| 139 | inside surface, arcuate | |
| 140 | electrode | |
| 141 | body, insulating | |
| 142 | tip, distal | |
| 143 | slot, reinforcing tube | |
| 144 | joint, tip | |
| 145 | interliner sleeve | |
| 146 | opening, interliner | |
| 147 | insert | |
| 148 | cross hole | |
| 149 | weld | |
| 150 | termination side, insert | |
| 151 | weld side, insert | |
| 152 | slot, insert | |
| 153 | shoulder, insert | |
| 154 | chamfer | |
| 160 | insert, tubular | |
| 161 | insert body, tubular | |
| 162 | necked portion, insert | |
| 163 | hole, insert | |
| 164 | electrode | |
| 165 | arcuate cutout, electrode | |
| 166 | cross hole | |
| 167 | weld | |
| 168 | insert, arcuate | |
| 169 | insert, partly tubular | |
| 180 | cannula | |
| 182 | distal end, cannula | |
| 183 | proximal end, cannula | |
| 184 | outer surface | |
| 185 | central lumen | |
| 186 | slot, cannula | |
| 187 | collar | |
| 190 | cannula, stepped lumen | |
| 191 | portion, distal, cannula | |
| 192 | lumen, enlarged | |
| 200 | the brain | |
| 201 | stereotactic arc | |
| 202 | guide holder | |
| 203 | stop holder | |
| 204 | instrument carrier | |
| 205 | burr hole | |
| 206 | skull | |
| 207 | guide, cannula | |
| 208 | bushing, stop | |
| 209 | lead | |
| 210 | stylet means | |
| 211 | handle | |
| 212 | connector, test | |
| 213 | scale, sliding arm | |
| 214 | marks, stylet sleeve | |
| 215 | screw, handle | |
| 216 | screw, stop | |

-continued

| | |
|---|---|
| 217 | peel feature |
| 220 | microdrive |
| 221 | microelectrode holder |
| 222 | carriage, microdrive |
| 223 | lead screw |
| 224 | micrometer scale |
| 225 | scale, frame |
| 226 | sleeve |
| 227 | screw |
| 228 | conductor, microelectrode |
| 229 | proximal end, microelectrode |
| 230 | handle |
| 232 | sleeve, protective |
| 240 | retentive portion, sheath |
| 241 | cutting thread |
| 242 | loop |
| 243 | weakened section |
| 244 | cutting thread |
| 245 | weakened section |
| 250 | cable, peelable portion |
| 251 | stylet |
| 252 | attachment location |
| 253 | sheath |
| 254 | slit, sheath |
| 255 | stylet portion |
| 260 | cable portion |
| 261 | slot, stylet |
| 262 | stylet |

DETAILED DESCRIPTION

Glossary

In the ensuing description and claims, the following terms have the meanings indicated.

"Lead" encompasses a stimulation lead, a sensing lead, or a combination thereof, intended for a chronic implantation.

"Probe" refers to a testing electrode or a recording microelectrode with a very small active area, used to sense and record electrical signals from individual cells or very small cell regions.

"Stylet means" encompasses solid rod stylets, multi-section stepped stylets, tubular stylets or a combination of these, and accessories such as sleeves and handles, providing the requisite stiffness to the lead, and travelling with the lead, when the lead is advanced into the tissue.

"Lead introduction" refers to the procedure of implanting the lead, including use of temporary electrode probes for physiological mapping of the target site and test stimulation, required to verify electrode localization and to confirm a desired therapeutic effect.

"Introduction tools" refers to the tools, adapters, and accessories used to accomplish the lead introduction procedure.

"Trajectory" refers to a straight path through the tissue to the intended target, as defined by lead introduction tools.

"Target" refers to the ideal or optimal location for lead electrode implantation, as determined by imaging and/or physiological mapping.

"Proximal" and "distal" use a device or an external instrument as the reference, i.e., "proximal" means proximal to the device and "distal" means distal from the device. Similarly, a proximal direction is the direction toward a device and a distal direction is the direction away from the device and toward the target tissue.

FIGS. 2-16C—Leads with Cable Merging into Sheath Wall

Traditional iso-diametric leads are designed to be passable through a cannula so that the cannula can be removed after the lead is successfully localized in the target tissue. An iso-diametric lead typically has coiled conductors with a stylet accommodated within the central opening (lumen) of the coils. The stylet is relatively thin (approx. 0.4 mm diameter) and relies on a brain-entering cannula to provide additional stiffness necessary to maintain the stylet's pointing accuracy. The lead can be very long (400 mm or more) to satisfy the requirements of the introduction tools, as discussed in the prior art section above. The iso-diametric lead construction is thus in large measure constrained by the use of coiled conductors and by the requirements of the associated lead introduction tools and methods.

The disclosed leads and the associated introduction tools and methods remove the traditional constraints on the lead construction. In particular, a slotted cannula (disclosed in a separate section below) allows decoupling of the conductor cable and the proximal connector from the lead introduction tools. In the disclosed lead-cannula system the lead does not need to be passable through the cannula, thus allowing each functional portion of the lead to have a different cross-sectional profile and to be adapted for a particular need.

FIG. 2 is a perspective view of an embodiment of a variable section (non-iso-diametric) lead 20 shown side by side with a cooperating stylet 40. The lead has a proximal end 21 and a distal end 22. The lead comprises an electrode terminal 23 having a body 24 and at least one electrode 25 at the distal end, a connector terminal 26 having a body 27 and at least one contact 28 at the proximal end, and a conductor cable 29 having an insulating body 30 and at least one conductor 31 (FIG. 4) electrically connecting at least one electrode to at least one contact.

The distal portion of the lead further comprises a substantially tubular sheath 32 having a predetermined length and a wall thickness, and extending from the electrode terminal body in the proximal direction. The sheath has a proximally facing opening 33, an outer end 34, and an outside surface 35.

The electrode terminal, the sheath, the cable, and the proximal connector may have different cross-sectional profiles and can be independently optimized for their function. Thus the electrode terminal can be desirably small, the sheath can be designed to accommodate a substantial stylet, the cable can be desirably short and constructed to provide both flexibility and crush resistance, and the proximal connector can have any desirable mating configuration. The above functional portions of the lead can be merged together in a variety of ways. In particular, different ways of merging the cable portion with the other portions of the lead will be disclosed. In the lead embodiment discussed in this section (FIG. 2) the cable merges into the sheath's wall 36, which may be locally thickened, and the conductors extend to the respective electrodes within the sheath wall.

The electrode terminal and at least a portion of the sheath are designed for introduction into the brain. The outside surface of the electrode terminal is preferably iso-diametric with a predetermined outside diameter, but can be of any shape forming a smooth outside surface. The smooth surface minimizes traction when passing through the tissue or a cannula and to mitigate an adverse long term tissue reaction.

The outside surface of the sheath is also smooth and substantially cylindrical and is preferably contiguous with the outside surface of the electrode terminal body. The electrode terminal and the sheath of lead 20 are shown having the same outside diameter, but the diameters need not necessarily be the same. Specifically, it may be desirable to make the diameter of the electrode terminal smaller than that of the sheath, as shown in FIG. 14, in order to optimize it for smaller anatomical targets.

When the lead is fully implanted, it may be desirable that the outer end of the sheath is outside of the cranium (e.g., to provide a smooth surface for contact with the brain tissue and to enable anchoring of the sheath at the burr hole). In such case, the combined length of the electrode terminal and of the sheath should be greater than the maximum depth of any of the contemplated anatomical targets in the brain. In other cases, e.g., when the only function of the sheath is to accommodate the transition of the cable into the electrode terminal, it may be desirable to make the sheath shorter and thicker so that it becomes essentially an integral part of the electrode terminal body having an outer end 34.

The connector terminal body is shown in a "paddle" configuration which can be used with a variety of implantable connectors, including those disclosed in my co-pending patent application Ser. No. 12/187,392, filed on Aug. 7, 2008.

Stylet 40, shown separated from the lead, has a distal portion 41, a body portion 42, and a step 43. Stylet body 42 cooperates with sheath opening 33.

Figure 3:
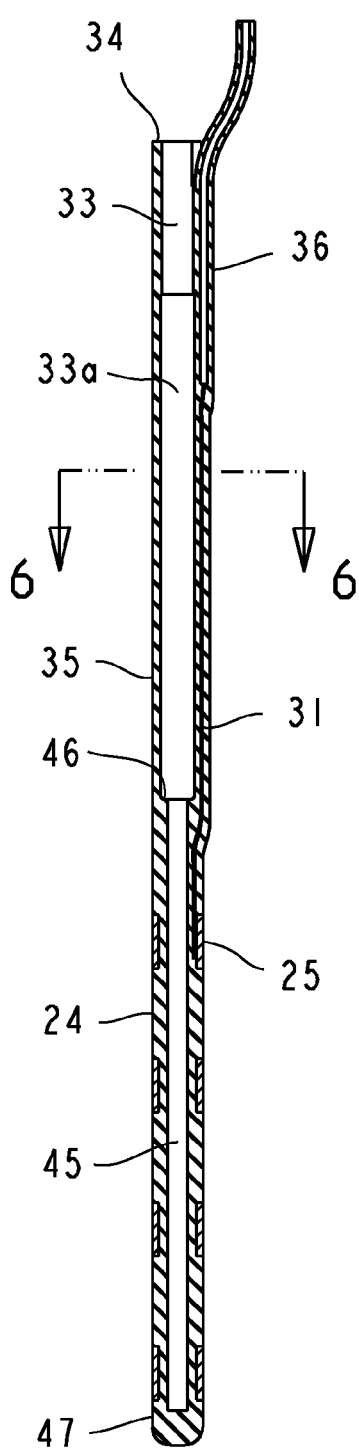
FIG. 3 is a cross-sectional view of the lead of FIG. 2, taken at the cable, as indicated by the lines 3-3 of FIG. 2.

FIG. 3 shows one of many possible cross-sectional configurations of cable 29. Conductors 31 are loosely fitted in the lumen of insulating body 30. The axial length of each conductor can be greater than the axial length of the cable body, so that no axial tension is applied to a conductor when the cable body is stretched to a length not exceeding the length of the conductor.

Stranded conductors (i.e., having multiple wire strands twisted together) are shown but single-strand conductors or other known multi-strand conductor constructions can be used. The wires can be made from platinum-iridium alloy or other high tensile strength alloy suitable for use in chronic stimulation leads. The diameter of individual wire strands may be 0.025 mm (AWG 50), 0.032 mm (AWG 48) or other desirable size.

The individual wire strands may have a coating of insulating material, such as ethylene-tetrafluoroethylene (ETFE) or other fluoropolymer, polypara-chloroxylylene (sold under the trademark Parylene-C by Specialty Coating Systems, Indianapolis, Ind.), or other insulating material used for coating of implantable conductors. Multi-strand conductors may have additional collective coating or extrusion of insulating material to hold the multiple strands together. Alternately, bare multi-strand conductors may have only a collective insulation which may be coated or co-extruded onto the conductors.

In an exemplary construction, utilizing 0.025 mm diameter wires, a three-wire stranded conductor may have a diameter of approximately 0.1 mm, including insulation. The overall diameter of a four-conductor cable can be 0.5 mm or less.

The length of the cable can be advantageously short since the cable does not interact with the lead introduction tools. With the shorter and thinner cable, the overall length and volume of the lead are significantly reduced. This is in contrast to the iso-diametric leads of the prior art which may have an outside diameter of 1.3 mm and a length of 400 mm, the length dictated in large measure by lead introduction needs. The short cable length of disclosed cables also helps to mitigate the high cost of precious metals and alloys such as platinum-iridium, which are desirable conductor materials for neurostimulator leads.

Figure 4:
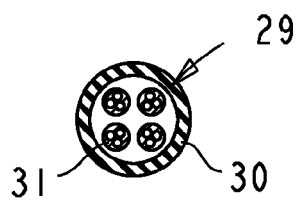
FIG. 4 is an alternate cross-sectional view of the cable.

FIG. 4 shows a variation of cable construction with an insulating body 44 having a flattened cross-sectional profile. The conductors are arranged in a single row, in a flat cable fashion. Such construction may be useful at the entrance of the cable into the sheath or within the sheath. The transition from a round to a flat profile can be made within cable-to-sheath merging area 36 or at any other section of the cable, e.g., before the entry of the cable into the sheath. If desired, the cable may have a flattened configuration throughout its entire length.

Figure 5:
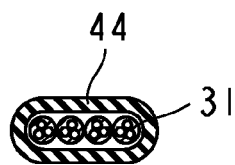
FIG. 5 is a partial cross-sectional view of the lead of FIG. 2, taken along the lead's longitudinal axis.

FIG. 5 is a longitudinal cross-sectional view of lead 20 and shows features of the sheath opening accommodating stylet 40. The portion of sheath opening 33 adjacent to outer end 34 is sized for a slight interference fit with stylet body 42. The interference fit, or "retentive fit", retains the sheath on the stylet body. The remaining portion 33a of the sheath opening is sized for an easy sliding of the stylet to allow withdrawal of the stylet from this portion of the sheath with a minimum of traction. Lumen 45 in the electrode terminal is sized to slidably accommodate the stylet's distal end portion 41. The lumen extends to a distal tip 47 which is shown as an integral part of the insulating body of the electrode terminal. Bottom 46 of the sheath opening provides a bearing surface for step 43 of the stylet.

FIG. 5 also illustrates tangential entry of cable 29 into the sheath at 36 and routing of a conductor 31 to an electrode 25.

Figure 6:
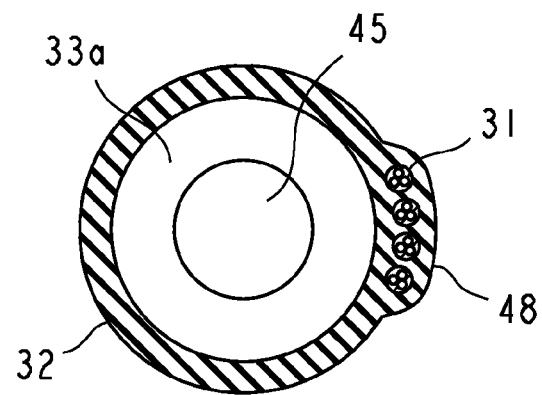
FIG. 6 is a cross-sectional view of the lead of FIG. 2, taken at the sheath, as indicated by the lines 6-6 of FIGS. 2 and 5.

FIG. 6 shows a cross-section of the sheath. The conductors are arranged on one side of the sheath within a locally thickened wall 48.

Figure 7:
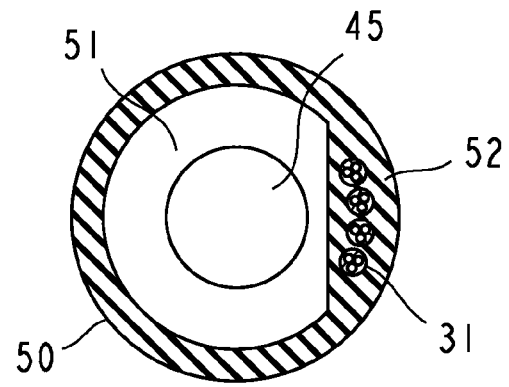
FIG. 7 is a cross-sectional view of an embodiment of a lead having tangentially exiting cable and a true circular sheath exterior.

FIG. 7 is a cross-sectional view of a variation of the sheath's cross-sectional profile wherein sheath 50 has a D-shaped opening 51. The conductors are arranged within a thickened sheath wall 52, but the wall is thickened in the inward radial direction, i.e., at the expense of the sheath opening. The outside of the sheath can thus be cylindrical all around. Other sheath profiles can be used, including a combination of the two discussed above wherein a nominally cylindrical wall is locally thickened in both inward and outward radial directions. In such case, the inward thickening or protrusion can be used to create a retentive fit on stylet portion 42.

Figure 9:
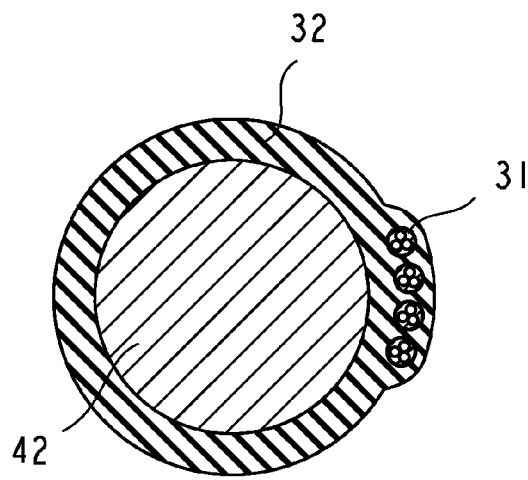
FIG. 9 is a cross-sectional view of the lead-stylet assembly of FIG. 8, taken near outer end of the sheath where the stylet is retentively engaged with the sheath, the view taken as indicated by the lines 9-9 of FIG. 8.
Figure 10:
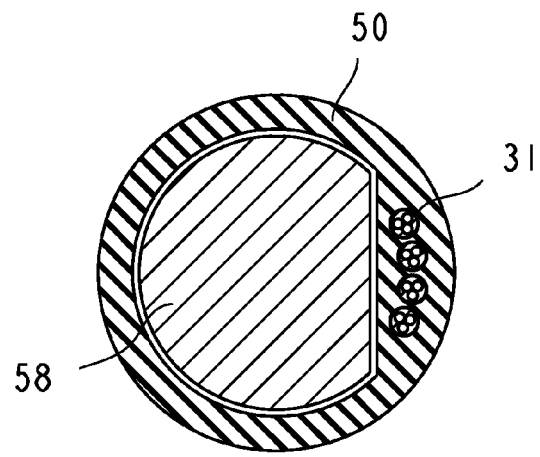
FIG. 10 is a cross-sectional view of an alternate lead-stylet assembly, taken at the sheath where the stylet is slidably engaged with the sheath.

FIGS. 8-10 are the cross-sectional views of FIGS. 5-7 with stylet means installed. Since the conductors are not present in the sheath opening, a substantial cross-section for the stylet is available. In a lead having an outside diameter of 1.3 mm or less, the thickness of the sheath insulation can be approximately 0.15 mm, thus maximizing the space available for the stylet. (If a larger diameter cable is desired, the wall thickness allowance can be increased.) The stiff stylet can provide the requisite stiffness to enable introduction of the lead into the brain without cannula entering the brain.

The stylet body is retentively engaged with the proximal portion of the sheath by slight interference fit as indicated by the surface-to-surface contact between these components in FIG. 9. Alternately, or in addition to slight interference, a shearable adhesive interface can be used to provide the desired retention between the stylet body and the distal portion of the sheath. Outside the retention area, the diameter of the sheath opening is slightly larger than the diameter of the stylet body, allowing removal of the stylet with minimal traction on the sheath after the retention mechanism is released.

The retentive engagement of the stylet with the sheath assures positive translation of the lead with the stylet, that is not affected by the compressibility of the lead or by the traction between the lead and the introduction tools. The lead can also be steered rotationally which may be desirable for directional electrode configurations. Since the stylet must provide both advancement and retraction of the lead, the retentive force must exceed maximum traction on the lead when the lead is being retracted, to prevent an unintended release of the lead from the stylet during retraction.

The distal portion of the stylet is received in lumen 45 of the electrode terminal. The stylet's distal portion is shown extending to the lead's distal tip 47, but without contacting the tip. Since the stylet is supported at the bottom of the sheath, distal tip 47 does not need to be engaged by the stylet.

In conventional lead designs, such as lead 10 of FIG. 1, the stylet may come in contact with the distal tip of the lead. This imposes significant structural constraints on the tip design, which must be suitably reinforced. In addition, an external stylet retainer is used on the proximal end of the lead to couple the stylet with the lead in order to prevent disengagement of the stylet when the lead is being retracted.

In the disclosed design, the distal tip of the stylet does not bear on the distal tip of the lead. Having alternate support areas relaxes the tip structural requirements and allows lumen 45 to be extended through the tip, e.g., to allow use of a microelectrode. Also in contrast to the conventional iso-diametric leads, the retentive fit between the stylet and the sheath provides a self-contained retention mechanism (no additional parts, such as a stylet retainer) and minimizes internal lead displacements due to traction and axial compressibility and/or stretchability of the lead.

FIG. 8 shows a stylet sleeve 55. The sleeve's distal end 56 is in contact with the outer end of the sheath, and constrains the lead from retracting with the stylet when the stylet is being removed. The distal end of the stylet sleeve may bear on the outer end of the sheath when the lead is being advanced.

The stylet is slidably received in the inner lumen of the stylet sleeve. By holding the outer end of the sheath in place and retracting the stylet, the sheath can be released from the stylet. This functionally facilitates lead introduction and minimizes dislodgment of the implanted lead due to removal of the insertion tools.

The D-shaped opening in the sheath of FIG. 10 receives a stylet body 58 with a correspondingly D-shaped profile. The cross-sectional view of FIG. 10 is taken at the sheath in the non-retentive portion of the sheath, as indicated by the clearance fit of the stylet in the sheath opening.

Figure 11:
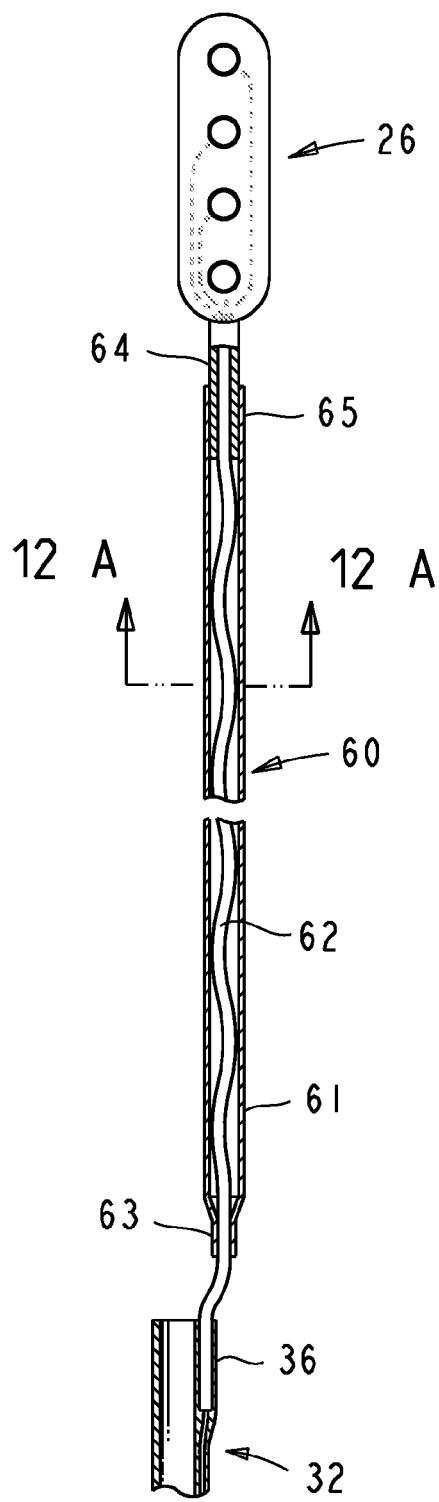
FIG. 11 is a partial cross-sectional view of a lead having a wavy cable incased in a sleeve, the view taken along the lead's longitudinal axis, the cable shown interfacing with the connector terminal and the sheath.
Figure 12:
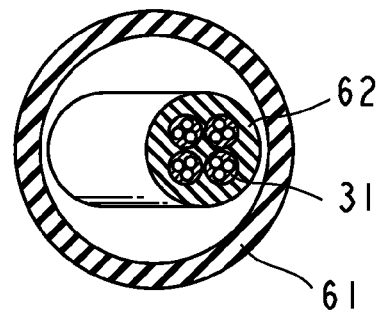
FIG. 12A is a cross-sectional view of a wavy cable, as indicated by the lines 12A-12A of FIG. 11.
FIG. 12B is a cross-sectional view of an alternate wavy cable having conductors arranged into a ribbon.
Figure 12:
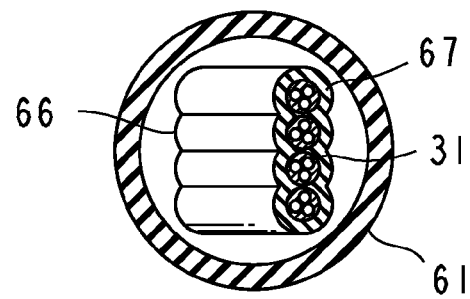
Figure 13:
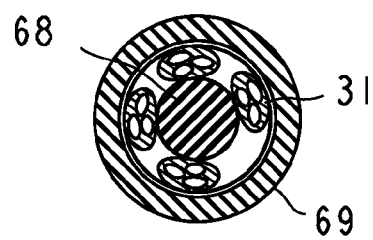
FIG. 13 is a cross-sectional view of an alternate cable construction with conductors helically wound onto an elastomeric core.

FIGS. 11-13 show several alternative cable constructions. Without cannula and stylet restrictions, many cable constructions and conductor types are possible. In particular, stranded conductors can be employed. Cables constructed with stranded conductors have good flexibility and, in contrast to coiled conductors commonly used in implantable leads, provide better crush and kink resistance, and a small minimum bend radius (important at the lead exit from the burr hole and at the entry to the proximal connector). The stranded conductors also have greater flexibility and higher tensile strength than single conductors having equivalent cross-section.

In FIG. 11, a cable embodiment 60 has a wavy form and is encased in casing 61. As shown in FIG. 12A, cable body 62 can have a smaller outside diameter and conductors 31 can be closer together than in the straight cable 29 of FIG. 3, since the additional service length is provided by the waviness of the cable.

The wavy form can be sinusoidal, helical, irregular, or any combination that can provide an additional axial service length within the casing, allowing the cable to have stretchability in service. Such stretchability allows accommodation of movement and or tissue dislocation (e.g., due to atrophy or growth), and thus prevents build up of axial tension in the lead which could cause lead dislodgement.

The waviness may be imparted to cable body 62 by molding, heat forming, or other methods. A thermosetting insulation material, such as silicone rubber, can be molded to a wavy shape while in a green (uncured) state and subsequently cured. In the case of a thermoplastic insulation material, such as a polyurethane, the cable body may be made wavy by molding into desired form or by heat forming a straight cable into a wavy form. Alternatively, a straight cable can be fed into casing 61 so that a random waviness is obtained. Casing 61 can be a discrete tubing made from silicone rubber, polyurethane, or a similar elastomeric material. Casing 61 can be sealed onto the cable's insulating body 62 at distal end 63 and can also be sealed onto the connector terminal sleeve 64 at proximal end 65.

A shorter, thinner, more flexible and crush resistant cable is more robust and easier to manage intra-operatively. For example, the cable may be coiled into a small coil or arranged into a service loop adjacent to the burr hole without causing concerns about cable crossing on itself.

FIG. 12 B shows a wavy cable embodiment 66 having a ribbon configuration. Insulation 67 can be co-extruded onto either bare or pre-insulated conductors 31. The flattened cross-sectional profile facilitates merging of cable 66 into the sheath at 36.

FIG. 13 is another embodiment of a cable, having conductors 31 helically wound around an elastomeric core 68 and placed in an insulating sleeve 69.

FIGS. 14 and 15A-B show an embodiment of a small-dimensioned electrode terminal 70 with closely spaced electrodes 71. Such small-dimensioned electrode terminal is desirable for implantation in a small and/or dense anatomical target where high spatial resolution is required for electrode localization. As a non-limiting example, the electrode terminal's diameter may be 1.0 mm, the electrode's length may be 1.0 mm, and the electrode pitch may be 2.0 mm. The sheath's construction and size can be substantially the same as in lead 20. The electrode material can be platinum, platinum/iridium, or the like.

The electrode terminal has a reinforcing tube 73 which extends from the distal end of the terminal to the bottom of sheath opening 33a. The reinforcing tube is shown having an integral tip 74 and a lumen 75 designed to receive a stylet (e.g., distal portion 41 of stylet 40) and/or to slidably guide a microelectrode probe. The proximal end 76 of the reinforcing tube is flush with bottom 46 of the sheath opening to provide a stable bearing surface for stylet step 43. Alternately, distal tip 74 may be a separate part joined to the tube or molded over the tube as part of the electrode terminal insulating body 72. While the above described construction is advantageous for small-dimensioned electrode terminals, it is also applicable to standard size electrode terminals, such as in lead 20.

If the reinforcing tube is made from a conducting material, the tip may form at least a portion of the most distal electrode or may provide a separate tip electrode. Such tip electrode can be connected to a corresponding contact of the proximal connector and used as one of the device's electrodes. Alternatively, the tip electrode may be dedicated for use with a recording microelectrode and/or for test stimulation.

The conductors are terminated to respective electrodes using inserts, as will be explained in a separate section below. Conductor 31 is joined to an insert 77 which in turn is joined to an electrode 71, preferably by welding at cross hole 78 (better seen in FIG. 16C).

FIG. 15B is the cross-sectional view of FIG. 15A with a stylet installed. The stylet is substantially the same as stylet 40, with the distal portion having a diameter and length adapted to slidably fit in lumen 76. Stylet step 43 is in contact with the proximal end of reinforcing tube 73. The distal tip 79 of the stylet may protrude from the opening in the distal tip of the lead and may be rounded to minimize disruption of the tissue along the insertion trajectory.

FIGS. 16A-C show the distal portion of the lead with a stylet means adapted for introduction of a microelectrode probe. A tubular stylet 80 is installed in the sheath opening so that the stylet's distal end is at the bottom 46 of the sheath opening and in contact with the proximal end of the reinforcing tube. The tubular stylet and the reinforcing tube form a continuous lumen which slidably accommodates a microelectrode probe 81. The microelectrode probe can be pre-inserted into the lead so that the distal tip 82 of the microelectrode extends a desired distance from the distal tip of the lead, and the lead with the microelectrode can be advanced to a predetermined location above the target. Using introduction tools described in connection with FIGS. 50 and 51, the microelectrode probe can be advanced or retracted in unison with the lead or independently from it.

The body of the microelectrode probe couples the stylet and the reinforcing tube and thus helps to maintain the stylet and the reinforcing tube in a coaxial relationship. The coupling constrains the electrode terminal to be co-linear with the stylet and thus helps to maintain the lead on the insertion trajectory defined by the lead introduction tools. If the body of the microelectrode does not have an adequate stiffness, an additional stylet can be used in place of the microelectrode to advance the electrode terminal to the desired initial location.

FIG. 16B shows an alternate coupling mechanism between the stylet and the reinforcing tube. The reinforcing tube 73a extends into the sheath opening and is accommodated in a counterbore 83 of stylet 80a. The reinforcing tube is thus directly coupled to the stylet and is constrained by the counterbore in the stylet to be substantially co-linear with the stylet. Since the coupling does not rely on the microelectrode, a thinner microelectrode probe can be used. The direct coupling is in effect even if the microelectrode lead is not present, which provides more flexibility in the lead introduction procedure. For example, the microelectrode probe can be introduced after the lead is pre-inserted into the brain or omitted altogether from the procedure. (However, for applications not requiring the use of a microelectrode probe a solid stylet shown in FIG. 15B may be preferred.)

FIG. 16C is a magnified cross-sectional view of the most distal portion of FIG. 16A, to show more clearly the longitudinal cross-section of microelectrode lead 81. A conductive core 85 has a thin layer of insulation along its length, except for a very small area on the distal tip which is exposed to provide the active microelectrode site. A stiffening tube 86 is installed over the core and an inner insulation 87. An outer insulating tubing 88 is applied over the stiffening tube and the transition between the tubing and the core is smoothed with an adhesive 89. A microelectrode probe with a stiffening tube is desirable where the probe is used to couple the stylet with the electrode terminal as shown in FIG. 16A.

Microelectrodes are available in a variety of materials and constructions from Micro Probe, Inc. of Maryland, USA. The core wire is typically a platinum-iridium or tungsten, the core's insulative coating is a thin layer of polypara-chloroxylylene (Parylene-C), the stiffening tube is stainless steel and the outer tubing is polyimide. Stainless steel reinforced microelectrode probes are available with outside diameters ranging from 0.36 mm 0.61 mm.

Microelectrode probes without a stainless steel stiffening tube can have an outside diameter smaller than 0.36 mm and are suitable for use with a stylet means such as shown in FIG. 16B, where the microelectrode probe does not serve as a coupling between the stylet and the electrode terminal.

While use of the microelectrode probes was illustrated in connection with the small-dimensioned (i.e., smaller outside diameter and closer electrode spacing) electrode terminals, the microelectrodes can also be employed with lead 20. In such case, the distal tip 47 will have a through hole, and stylet 40 will have a central lumen throughout its entire length to accommodate the microelectrode probe. The lumen does not need to be of a constant diameter throughout. It is sufficient that a lumen in the distal portion 41 provides a sliding guidance for the microelectrode probe. Such stylet with a central lumen can be constructed from two nested tubular segments.

FIGS. 17-25—Termination of Conductors to Electrodes Using Inserts

An important aspect of fine lead construction and fabrication is the termination (connection) of conductors to electrodes. A direct termination of coiled conductors to ring electrodes is well known in the art. Each coiled conductor needs to be unwound from the coil, bared at the end, and routed to a respective electrode where it is welded in a small groove adjacent to the outer surface of the electrode. However, the presently practiced termination techniques are difficult when lead diameter is less than 1.0 mm and electrode spacing is less than 2.0 mm. In addition, a very small joint adjacent to the electrode's outer surface is fragile and susceptible to damage due to flexing or buckling of the lead. While further miniaturization of leads is desired, a direct termination of finer or stranded conductors is even more problematic and in need of solution. Using inserts as described below provides a robust method of terminating the conductors to electrodes and facilitates the lead fabrication.

The inserts are particularly advantageous for termination of stranded conductors, allowing the conductors to be joined easily and reliably to the relatively large area of the insert. The insert and the electrode can be designed to nest together to facilitate their alignment and joining and to promote an efficient use of available space.

The inserts can be made from materials used for the electrodes such as platinum or platinum-iridium, and economically produced by coining, stamping, or machining FIGS. 17-20 demonstrate use of arcuate inserts. Insert 77 has a generally arcuate form with an inner surface 91, an outer surface 92, a front edge 93 and a back edge 94. The end of conductor 31 is stripped of the insulation to provide a bare section 95 which is joined to the insert at inner surface 91. The conductor ends can be bared by mechanical stripping, laser ablation, or any known method that cleanly and neatly removes insulation from fine wires. The large attachment area enables a robust joint and makes it possible to use a variety of termination techniques. Stranded or solid conductors can be terminated by any known method used for stranded or solid conductors including laser or resistance welding, soldering, thermosonic bonding, crimping, and conductive adhesive bonding. After joining, the conductor-to-insert joint may be strain-relieved by encapsulating or coating the joint with an adhesive.

The conductor-insert assembly of FIG. 17 can be fabricated apart from the electrodes and other lead components. The required number of conductor-insert pairs can be assembled in a pre-determined arrangement consistent with the electrode spacing in the lead. The conductor-to-insert terminations can be easily inspected and tested. The thus prepared conductor-insert harness is nested with the electrodes as shown in FIG. 18, and the outer surface of each insert is joined to a respective electrode 71.

Figure 19:
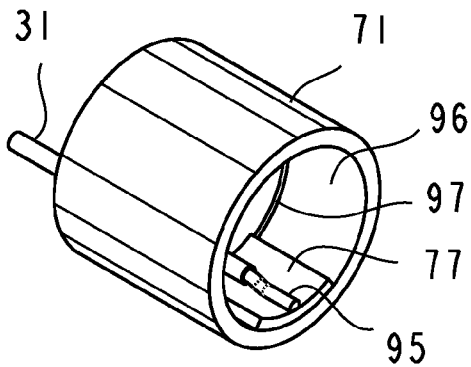
Figure 19:
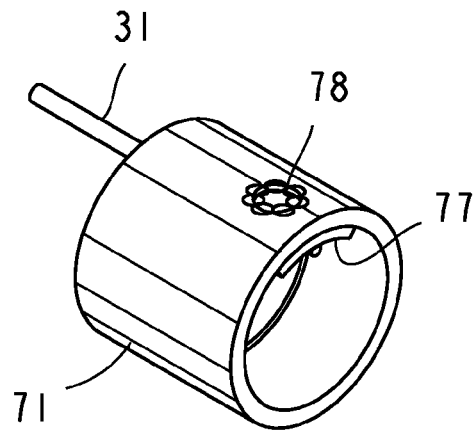

FIGS. 19 A-B show insert-to-electrode joint in greater detail. Electrode 71 is counterbored to form a recessed surface 96 and a step 97. The outer surface of the insert and the recessed surface of the electrode have complementary curvatures and can be nested together. Step 97 can be used to locate the back edge of the insert. FIG. 19B shows the insert joined to the electrode at cross-hole 78, e.g., by laser welding.

Alternatively, the insert may be joined to the electrode as shown in FIG. 20A-B. The insert is placed in recess 96 so that front edge 93 of the insert protrudes beyond rim 98 of the electrode. The distance by which the insert protrudes from the electrode can be set by step 97. An outer surface 92 of the insert is then attached to the rim of the electrode by weld line 99.

FIGS. 21A-C show another embodiment of an insert and a method of assembly. An insert 101 is in a form of a blank, designed to be accommodated in a complementary cutout 102 in an electrode 103. The insert has an inner surface 104, an outer surface 105 and a back edge 106. The remaining edges 107 of the insert are profiled to match the cutout in the electrode. The conductor is attached to the inner surface 104 using one of the methods listed for the arcuate inserts discussed above, e.g., laser welding.

The insert is joined to the electrode along cut-out 102, e.g., by laser welding. The resulting weld line 108 is shown in FIG. 21C. After attachment to the electrode, the outer surface of the insert is substantially co-planar with the outer surface of the electrode and back edge 106 of the insert is preferably aligned with the outer edge 109 of the electrode. If insert 101 is small, it does not need to have the same outer curvature as the electrode since the insert edges will be largely consumed by the weld line. It is desirable, however that the insert and the weld line are smooth and within the electrode's outside diameter.

FIG. 22 shows an insert 110 having a slotted portion 111 for captivating conductor 31. The slot holds the conductor for termination and provides a strain relief for the joint.

FIGS. 23 A-B show two stages of assembly of an electrode terminal utilizing inserts 101. The conductor-insert harness shown in FIG. 23A is pre-assembled as discussed above in connection with FIGS. 17-18. After the inserts are joined to the respective electrodes at 108, a reinforcing tube 73 and an insulating interliner 112 are added to obtain the assembly of FIG. 23B. The interliner can be a sleeve of an insulating material having a lengthwise slit, so that after it is placed on the reinforcing tube, a lengthwise opening 113 (shown in FIG. 23 filled with overmolding insulation) is created to accommodate the conductors. The interliner provides a thin layer of insulation which maintains the electrodes and the reinforcing tube in a coaxial relationship and helps to neatly arrange the conductors which are contained within the lengthwise opening. The interliner can be made from a thin polyimide tubing, with wall thickness approximately the same or slightly thicker than the outside diameter of the conductors, e.g., 0.1 mm or less. The interliner provides an effective way of introducing a thin and effective layer of insulation which would be impractical to obtain by other techniques, e.g., overmolding. Use of the interliner results in a compact electrode terminal construction and minimizes fixturing required for the assembly.

FIGS. 24-25 are cross-sectional views of a finished electrode terminal assembly. A body insulation 114 is added to fill the spaces between the electrodes and lengthwise opening 113 in the interliner sleeve. The material for electrode terminal body can be the same as the material of the sheath which may be silicone rubber, polyurethane, a silicone-urethane copolymer or the like. Other biocompatible polymers can also be used since, in contrast to the sheath and cable, the relatively short high definition electrode terminal does not need to be flexible. The insulation can be added by overmolding or, if a thermoplastic such as polyurethane is used, can be added in discrete form and heat-formed or heat-sealed in place.

Figure 26:
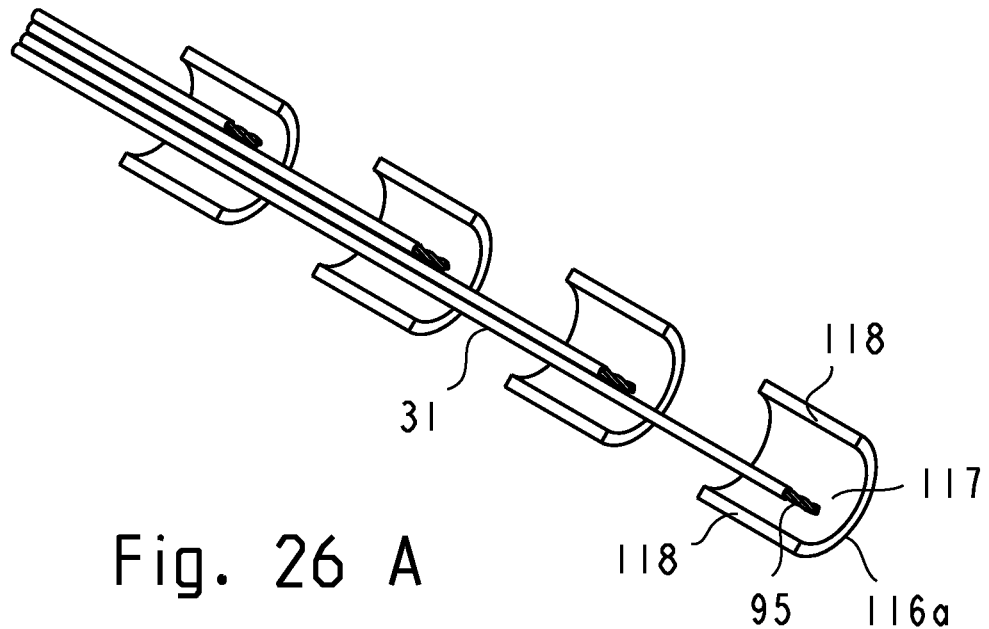
Figure 26:
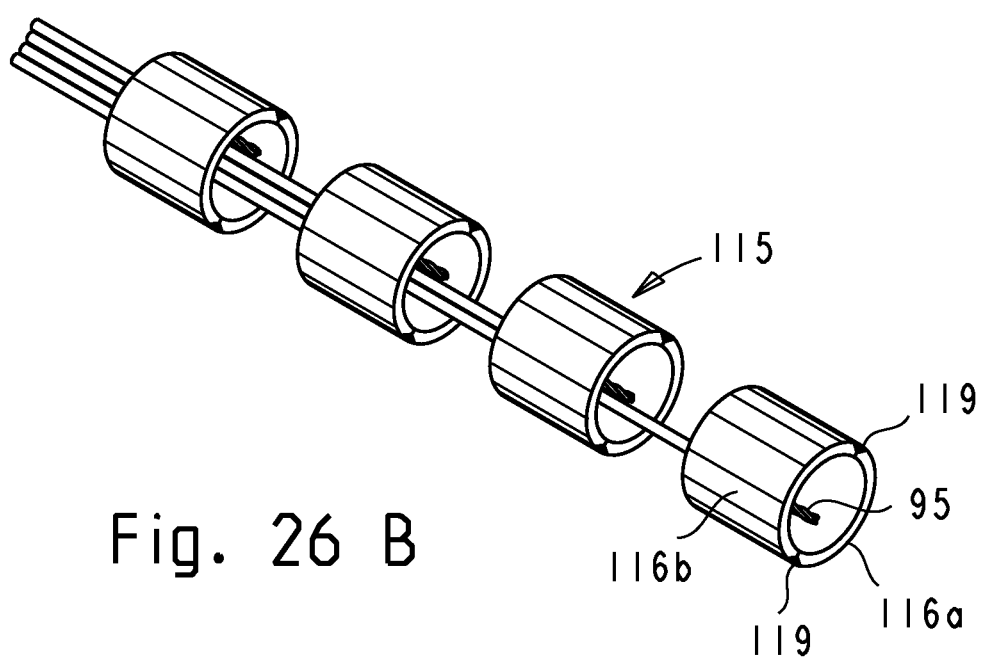

FIGS. 26 A-B show an embodiment of conductor-electrode harness, wherein the electrode 115 consists of two arcuate segments, preferably identical halves 116a and 116b. The conductor is terminated to an inner surface 117 of the first segment and the segments are then joined together along the corresponding longitudinal edges 118 to form a ring electrode. The weld lines are indicated by reference numeral 119. As in the case of the arcuate inserts discussed above, the ample and easily accessible conductor attach area enables many termination options and helps to achieve a robust joint. The conductor-electrode harness can be incorporated into any of the electrode terminal constructions discussed above.

Figure 27:
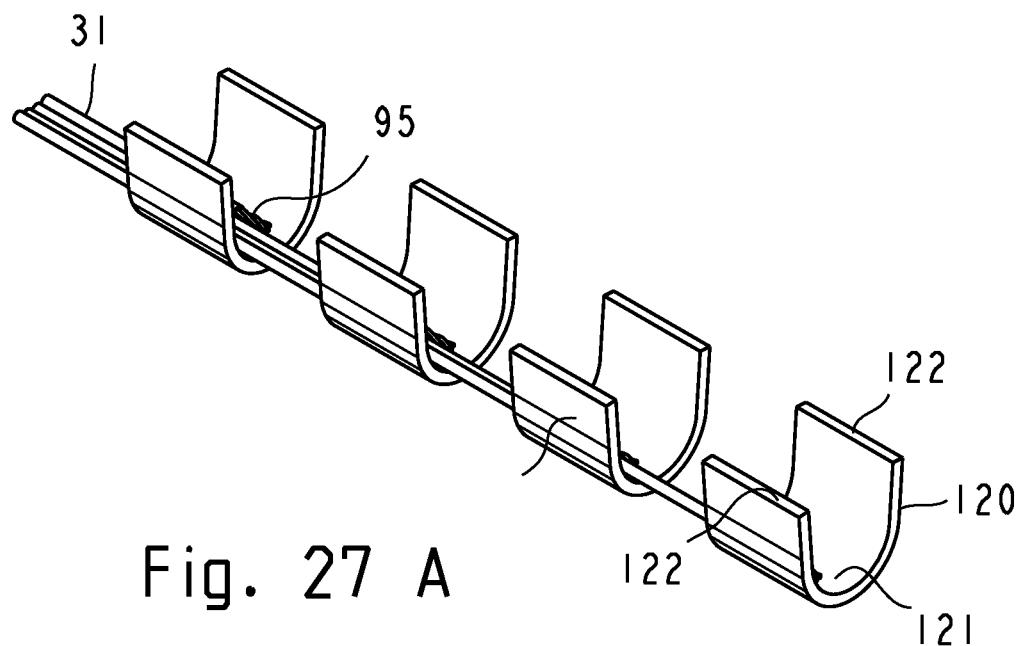
Figure 27:
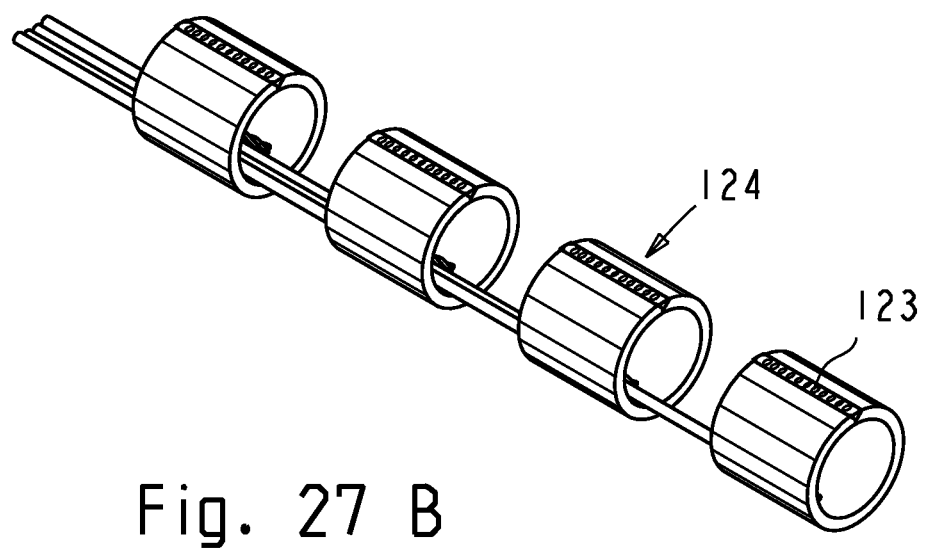

FIGS. 27 A-B show another embodiment of a conductor-electrode harness wherein conductors 31 are attached directly to partially formed electrodes 120. After the conductor is attached to the inner surface 121 of the partially formed electrode, the electrode is formed to the final tubular shape and the butting edges 122 are joined, preferably by laser welding, as indicated by weld line 123. The result is a ring electrode 124. The remaining electrode terminal components can be added to the harness either before or after the electrodes are formed to the final tubular shape.

FIGS. 28-32—Lead with Cable Merging into Electrode Terminal

In the lead embodiment disclosed below a conductor cable merges directly into the electrode terminal.

FIG. 28 is a perspective view of a lead embodiment 130 shown side-by-side with a stylet 131. The lead comprises a high resolution electrode terminal 132, a tubular sheath 133, cable 29 and connector terminal 26. Multi-conductor cable 29 enters sheath 133 through an opening 134 and extends inside the sheath opening toward electrode terminal 132.

Stylet 131 has a slot 136 to accommodate the centrally disposed cable 29. The most distal portion 137 of the stylet's slotted portion has an arcuate cross-section formed by counter-boring the distal end of the stylet. The arcuate portion 137 of the stylet is designed to engage a stiffening tube 138 extending into the sheath from the electrode terminal (FIG. 32).

FIGS. 29 and 30 are cross-sectional views of lead 130, with stylet 131 installed, taken at different depths of the sheath. The cross-section of FIG. 29, taken adjacent to the sheath opening 134 shows the slotted portion of the stylet in retentive contact with the sheath as indicated by a surface-to-surface contact between these components. Cable 29 is free to move in the slot and, once the cable is out of the sheath, it can be disengaged from the stylet completely and moved freely in a sideways direction. If desired, the cable can be retained within slot 136 by a slight interference fit through the lead introduction procedure and peeled away from the stylet before the stylet is removed.

The cross-section of FIG. 30, taken adjacent to the electrode terminal shows the arcuate portion 137 of the stylet in a sliding contact with the inside surface of the sheath, as indicated by a small clearance. In addition, the inside surface 139 of arcuate distal portion 137 of the stylet slidably engages the stiffening tube 138 extending from the electrode terminal.

FIGS. 31-32 show an embodiment of electrode terminal 132 comprising electrodes 140, insulating body 141, and distal tip 142. The outside diameter of the electrodes and the length and spacing of the electrodes are minimized to enable localization of the electrodes in the target tissue with high spatial resolution.

The cross-sectional view of FIG. 32 shows internal construction of electrode terminal 132 which is also applicable to any electrode terminal with a centrally exiting cable. The stiffening tube 138 provides a structural support for the terminal assembly. Tube 138 is preferably made out of high modulus material such as metal but can also be made from a reinforced hard polymer. The tube opening accommodates the conductors of cable 29 and, depending on the cable's outside diameter, may also accommodate a small portion of cable insulating body 30, as shown. The inside of the tube can be potted to form a relatively rigid core or can be filled with the insulating body material when insulating body 141 is formed. The optional potting is indicated by a dotted hatch in order not to obscure the internal construction of the electrode terminal.

The stiffening tube has a lengthwise slot 143 (better seen in FIG. 33) along the length adjoining the electrodes to provide a passage for the conductors, in order to allow them to be connected to respective electrodes 140. The distal tip 142 can be attached to the stiffening tube at 144 or formed as part of insulating body 141.

In addition to providing a small dimensioned and stable core for the electrode terminal construction, the stiffening tube also provides a means for coupling the electrode terminal to the stylet. The proximal end of the tube extends into the sheath opening so that it could be coupled to the arcuate end portion 137 of the stylet (FIG. 30). The coupling minimizes the deviation of the electrodes from the intended trajectory set by the lead introduction tools. Once the reinforced core is coupled to the stylet, the core becomes, in effect, an extension of the stylet and constrains the most distal portion of the lead from flexing. The length of the coupling should preferably be greater than five diameters of the reinforcing tube, or as required to assure a desired pointing accuracy for the distal end of the lead advancing through the tissue.

Exclusion of the stylet from the electrode terminal reduces the outside diameter of the electrode terminal and consequently the diameter of the electrodes. The lead can thus have a small-dimensioned electrode terminal without sacrificing the lead's pointing accuracy. The requisite stiffness is provided by the stiffening tube coupled to the stylet.

An insulating interliner sleeve 145 is installed over the stiffening tube. The interliner sleeve has a slit which forms a lengthwise opening 146 when the sleeve is wrapped around the stiffening tube (FIG. 33). The opening in the sleeve lines up with slot 143 in the stiffening tube to maintain a passage for the conductors.

Electrodes 140 are placed over the interliner tube, making a close fit, so that the electrodes are radially constrained relative to the core. This arrangement is space efficient and assures concentricity of the stiffening tube and the electrodes.

Each conductor can be terminated directly to the respective electrode but use of an insert provides many advantages as discussed above. Previously described inserts such as insert 77 or 101 and associated termination techniques can be used. However, other embodiments of an insert are introduced for this embodiment of the lead to demonstrate additional insert options.

An insert 147 is button-shaped and is accommodated in a cross-hole 148 (better seen in FIGS. 33-35) in the electrode, where it is joined to the electrode, preferably by a laser welding. The resulting weld area is shown at 149.

FIGS. 33-35 detail the insert construction and attachment to the electrode. Insert 147 is substantially round and has a wire termination side 150 and a weld side 151. The wire termination side may have a slot or channel 152 to facilitate receiving and joining a bared end 95 of conductor 31. A stranded three-wire conductor is shown but a single wire or any other known biocompatible conductor construction can be used. At least the weld side of the insert is substantially round and sized for close fit in cross-hole 148. The termination side is shown round and having a larger diameter than the welding side so that a shoulder 153 is created. The shoulder prevents penetration of the laser energy to the termination side of the insert and can be used to stop the insert against the inner surface of the electrode. However, the termination side does not need to be round or have a termination slot. In its simplest form the insert could be a cylindrical button with flat ends.

The insert can be made from a material similar or the same as that of the electrode, e.g., platinum-iridium alloy. The inserts can be fabricated by screw-machining, coining, or other efficient method.

In order to attach a conductor-insert pair to the electrode, the insert is brought into the opening of the electrode and is inserted into cross-hole 148. A chamfer 154 facilitates insertion of the insert into the cross-hole, and shoulder 153 provides a positive stop. The weld side of the insert may be slightly recessed below the outside surface of the electrode, as shown in FIG. 33, to assure that weld joint 149 does not protrude beyond the outer surface of the electrode.

FIGS. 36-38 show an alternate insert 160 which has a tubular body 161 with a necked portion 162 adapted for accommodating and crimping bared end 95 of conductor 31. The hole 163 is sized to receive insulated portion of the conductor in the body portion which may optionally be crimped to provide strain relief for the connection. In order to join the conductor-insert pair to an electrode 164, the body of the insert is nested in an arcuate cut 165 on the inside surface of the electrode and welded to the electrode at a cross-hole 166. The resulting weld is shown at 167.

FIGS. 39 and 40 show insert variations 168 and 169 respectively, that can be attached to electrode 164 in the manner similar to that described for insert 160, i.e., by nesting the insert in arcuate cutout 165 and welding at cross hole 166. Insert 168 is arcuate profiled throughout while insert 169 is partly arcuate and partly tubular. A bared conductor can be attached to these inserts by welding, soldering, conductive adhesive, or other known method.

Returning to the construction of electrode terminal 132 shown in FIG. 32, the conductor-insert harness can be prepared separately, i.e., apart from electrodes and other components. A desired length of conductors 31 is stripped of the cable's outer insulation and each conductor is cut to length according to the electrode spacing in the lead. The conductor ends are bared and terminated to the inserts. The inserts are thus disposed in a linear pattern and are spaced consistent with the electrode pitch.

FIGS. 41A-C show the electrode terminal at three stages of construction. In FIG. 41A the conductor-insert harness is inserted into the stiffening tube 138. Cable 29 is inserted into the stiffening tube either from distal or proximal end of the tube. If the cable is inserted from the distal end of the tube, the electrodes can be already attached, but the proximal connector 26 must not be attached and the cable must be passable through the tube, i.e., the cable diameter must not exceed the inside diameter of the stiffening tube.

In FIG. 41B, interliner sleeve 145 is added. The lengthwise slit in the interliner is aligned with the slot in the stiffening tube. If the stiffening tube is conductive, the slit in the sleeve is somewhat narrower than the slot in the tube, so that the inserts can be held in-line without contacting the stiffening tube. The electrodes are slipped over the interliner sleeve and aligned with the inserts. The inserts, with wires attached, are taken out of the tube through slot 143 and are inserted into the cross-holes of the respective electrodes where they are attached to the electrodes, preferably by a laser welding.

After all electrodes are in place, distal tip 142 is added and attached to the stiffening tube by an applicable method such as laser welding, ultrasonic welding, or adhesive. Finally, the electrodes are set by fixturing or other method (such as adhesive tacking) and the assembly is overmolded to form insulating body 141. The sheath may be formed concurrently with the overmolding operation. Alternatively, the sheath can be molded separately and fused to the body of the electrode terminal by heat sealing or similar process.

FIGS. 42-53—Lead Introduction Tools

The lead introduction tools are based on a slotted cannula which eliminates the need for the entire lead to be passable through the cannula's lumen. By allowing the cable to exit through the slotted opening on the side of the cannula, the main body of the cable and the proximal connector can bypass the cannula.

The slotted cannula is kept completely external to the brain. The relatively substantial stylet systems of the disclosed leads can be made sufficiently stiff to eliminate a brain-entering cannula.

FIGS. 42-43 show an embodiment of a slotted cannula 180 for use with the disclosed lead systems, such as the lead-stylet-sleeve assembly of FIG. 8, comprising lead 20, stylet 40, and stylet sleeve 55. The lead system components are shown inserted into the slotted cannula. The cannula has a distal end 182, a proximal end 183, a substantially cylindrical outer surface 184, and a central lumen 185. The cannula further has a lengthwise slot 186 originating at distal end 182, forming an opening contiguous with the central lumen.

The lead-stylet assembly is inserted into the cannula from the cannula's distal end. Cable 29, exiting from sheath 32, is aligned with the slot and traverses the slot as the lead moves in the cannula. The width of slot 186 is sized to accommodate the cable and the protrusion on the side of the sheath from which the cable emerges. (In the variation of FIG. 44, slot 186 needs to accommodate cable only.)

The length of the slot preferably exceeds the combined length of the lead's electrode terminal and the sheath so that both the electrode terminal and the sheath can be accommodated within the cannula when inserted from distal end 182. If desired, the slot may be extended through the entire length of the cannula, including a collar 187. In such a case, the lead-stylet assembly may be inserted into the cannula from either distal or proximal end.

The slot serves as a passage for the cable which moves along the slot as the lead is being advanced or retracted through the cannula. The edges of the slot adjacent to the lumen are rounded to allow a smooth movement of the cable within the slot. Optionally, the stylet can be keyed to the cannula to keep the cable centered in the slot.

Stylet tube 55 slidably couples stylet body 42 to the lumen of the cannula and facilitates dislodgement-free disassembly and removal of the lead introduction tools after the lead localization is finalized. In the embodiment of FIGS. 42-43, the outside diameter of the stylet sleeve matches the outside diameter of the sheath. The cannula's lumen is sized to slidably receive the distal portion of the lead as well as stylet sleeve 55. The stylet sleeve can be inserted into the cannula with the lead-stylet assembly or added after the lead-stylet assembly is already in the cannula. When assembled, distal end 56 of the sleeve is in contact with the outer end of sheath 32.

FIG. 44 is a cross-sectional view equivalent to FIG. 43, but with a lead-stylet assembly having sheath 50 with a D-shaped opening and a correspondingly profiled stylet portion 58, as shown in FIG. 10.

FIG. 45 is a variation of the cannula embodiment of FIG. 42, adapted for use with a thicker stylet sleeve. The cannula 190 has a stepped lumen. Since the stepped lumen is obtained essentially by counterboring the distal end of cannula 180, the same reference numerals are used to indicate features that are not changed by the counterbore. Thus the distal end portion 191 of the cannula has a lumen 185 sized to slidably receive and guide the lead's distal portion. The remaining length of the cannula has an enlarged (i.e., obtained by counterboring) lumen 192, sized to slidably receive and guide stylet sleeve 55. The cross-sectional view of FIG. 46 and the distal end view of FIG. 47 further illustrate the stepped lumen cannula configuration.

FIGS. 48A and 48B show a system for introduction of a lead into the brain 200, utilizing a stereotactic frame. As described in the prior art section, a stereotactic frame is typically used to identify the location of the lead entry into the brain and to facilitate the implantation of the lead. The stereotactic system is represented in FIGS. 48A-B by a stereotactic arc 201 which is attached to a stereotactic frame (not shown) which is rigidly mounted on the patient's head. The stereotactic arc has a guide holder 202 and a stop holder 203 which are slidably mounted in the instrument carrier 204. The stereotactic arc instrumentation, shown simplified, is a part of the Leksell® stereotactic system offered for sale by Elekta corporation (Stockholm, Sweden). The system is available with various accessories including a microdrive for precise movement of a microelectrode.

A stereotactic arc with appropriate target coordinates setting is used to select the location for a lead entry into the brain and is detached from the frame to allow preparation of the entry site. After a burr hole 205 in the skull 206 and an entry opening in the dura mater are created, a lead anchoring means (not shown) may be placed in the burr hole, and the stereotactic arc is re-attached to the frame.

Before re-attaching to the frame, the stereotactic arc is instrumented with a cannula guide 207 holding a cannula 180 and a stop bushing 208 by inserting them into the guide holder and the stop holder respectively. Lead 209 with stylet means 210 are inserted into the slotted cannula from the distal end of the cannula. Lead 209 can be any lead described herein. Stylet means 210 can be an individual stylet with a stepped diameter, a compound stylet constructed from tubular members or a combination of solid and tubular members, and any combination of a stylet and a stylet sleeve described herein. A solid rod stylet may be replaced with a tubular stylet wherein the central lumen of the tubular stylet is used to guide a microelectrode probe.

After the lead and the stylet means are inserted, handle 211 is placed on the stylet means so that when the handle arrives at the stop bushing the distal tip of the lead arrives at the desired location along the insertion trajectory, e.g., just above a predetermined location of the anatomical target in the brain. The desired stop location can be set knowing that, when the arc is attached to the frame, the target location corresponds to the center of the arc.

After the stereotactic arc is re-attached to the frame, the cannula is lowered so that the distal end of the cannula is just outside the skull. Since the cannula is completely external to the brain, it is advantageous to bring the distal end of the cannula as close to the skull as possible, even in contact with the skull. If desirable, the outside diameter of the cannula may be larger than the burr hole or the opening in the anchoring means to preclude the cannula from entering the brain.

As noted before, cable 31 and connector 26 bypass the introduction tools and thus can be optimized on their own merits. The cable length can be desirably short and the connector can have desired mating configuration. Decoupling of the cable and the connector from the lead introduction tools also allows the cable and the connector to be moved out of the away of the introduction tools. Connector 26 can thus be connected to an external recording or stimulation unit and may remain connected through various stages of the lead introduction procedure. The physiological responses to a test stimulation can thus be monitored during lead localization and disassembly and removal of the introduction tools.

If desired, an implantable device 212 (shown diagrammatically) can be connected to connector 26 of the lead without interfering with the lead introduction tools. Alternatively, device 212 can be permanently connected to the proximal end of the cable, wherein the conductors of the cable are directly terminated to the device's electrical feedthrough pins, i.e., without using a separable proximal connector 26. Elimination of separable connector interface reduces the size and the complexity of the device. Such smaller permanently attached device can be implanted adjacent to the burr hole, resulting in a very short cable length.

Only a relatively short portion of the lead, specifically the electrode terminal and the sheath, cooperates with the stylet and the lead introduction tools. The total length of the stylet is minimized and its cross-section is maximized. A sheath having 1.3 mm outside diameter can accommodate a stylet having up to 1 mm diameter, assuming a 0.15 mm minimum sheath wall thickness.

This is in contrast to the conventional iso-diametric leads and introduction systems where the entire length of a lead must cooperate with introduction tools. The conventional stylet is thin (e.g., it has a 0.4 mm diameter) and thus requires support of a brain-entering cannula. In addition, the long length and axial compressibility of the standard iso-diametric leads make them susceptible to lead placement errors and dislodgement due to traction at the long lead-cable-cannula interfaces. Such placement errors can only be exposed by additional physiological testing which lengthens the lead introduction procedure.

From the initial position shown in FIG. 48A, the lead is advanced along the insertion trajectory until the handle arrives at stop bushing 208. The stylet means can then be coupled to the stop bushing so that the lead could be advanced using a fine sliding motion of the stop holder. The lead is advanced in small incremental steps and an intra-operative test stimulation is performed to verify the desired response. The lead's current insertion depth may be indicated by a scale 213 on the sliding arm of the stop holder, indexed to a fixed reference mark on the instrument carrier. If desired, the stylet sleeve may also have graduated marks 214 (FIG. 50) to allow monitoring of the lead advancement into the brain relative to the stop bushing.

When a satisfactory localization is achieved and an effective and safe stimulation is confirmed, the insertion tools can be removed in a conventional way, i.e., by retracting the cannula to gain access to the lead at the exit from the burr hole, manually holding the lead at the exit from the burr hole, removing the stylet means, and anchoring the lead. However this process is prone to dislodgment of the lead from the confirmed efficacious localization. A more advantageous method will be disclosed next.

FIGS. 49A-B correspond to the FIGS. 48A-B respectively, but are enlarged partial views to show the lead introduction tools in a greater detail. Guide holder 202 and stop holder 203 slidably connect to the instrument carrier of the stereotactic arc as shown in FIGS. 48A-B. The lead introduction tools are shown cooperating with the lead-stylet-sleeve assembly of FIG. 8, i.e., having lead 20, stylet 40, and stylet sleeve 55. Cannula 180 is utilized. However, the tools and methods are applicable to any of the lead-stylet embodiments and cannulas described herein.

The lead-stylet assembly is inserted into the cannula 180 from the cannula's distal end and passed through the lumen in the cannula and through the center bore of stop bushing 208. Stylet sleeve 55 is slipped over the stylet body 42 so that the sleeve's distal end is in contact with the outer end of the sheath. Handle 211 is slipped over the stylet body and brought in contact with proximal end of the stylet sleeve. The handle is subsequently coupled to the stylet with a set screw 215 or other coupling means, such as a spring loaded coupling. The stylet sleeve is thus retained between the outer end of the sheath and the bottom side of the handle, and can move in unison with the lead.

Preferably, the length of the stylet sleeve is predetermined so that the distance from the distal tip of the lead to the proximal end of the stylet sleeve is a known system constant. This allows a user to easily reference the location of the distal tip of the lead to the intended target which is known to be at the center of the stereotactic radius.

From the initial position of FIG. 49A, the lead is advanced into the brain using the cannula as a guide, until the handle comes in contact with the stop bushing. When the handle stops at the bushing, the distal tip of the lead is at a desired pre-target location, typically slightly above the anatomical target in the brain. The stylet means may be now coupled to stop bushing 208 with a set screw 216 or other coupling means, such as spring loaded coupling, and incrementally advanced to the target using a fine motion of the stop holder or a microdrive (e.g., microdrive 220 of FIG. 50). The final lead localization in the target is performed using known techniques and is verified by a test stimulation.

When the lead localization is finalized, the introduction tools may be configured as in FIG. 49B. The stylet is still retentively engaged with the sheath and the outer end of the sheath is constrained by the stylet sleeve from retracting. After successful localization of the lead is confirmed to be efficacious, the remaining steps of the procedure must not alter the lead's position in the target. Specifically, a disassembly and removal of the lead introduction tools and the anchoring of the lead at the exit from the burr hole must not cause the lead to change position.

The stylet can be disengaged from the lead by simply pulling on the handle 211 to retract the stylet while the outer end of the sheath is still constrained by the distal end of the stylet sleeve. This releases the retentive grip of the outer portion of the sheath on the stylet. Since the lead is immobilized by the stylet sleeve when the stylet is retracted, the stylet is released without causing dislodgement of the lead.

Optionally, the cable may be designed to be peelable from the outer portion of the sheath at 217, so that a desirable length of the cable may be peeled away from the sheath thus producing a longitudinal break in the retentive area of the sheath. To facilitate the peel-away feature, a cutting thread can be provided or the peeling force can be applied directly to the cable. In the latter case, the portion of the cable that is subject to the peeling action may be reinforced, e.g., with a high tensile strength threads. In addition, the sheath may be weakened along the cut or peel lines. If desired, the cable may be peeled to the bone line or to an anchor so that it could be immobilized there before the cannula and then the stylet sleeve are removed.

If the cable does not have a peel-away feature, the disassembly of the introduction tools may follow these steps:

(a) Remove the stylet or retract until it is no longer in the portion of the sheath to be anchored.
(b) Raise cannula to provide access to the lead exiting the burr hole, preferably leaving a small outer portion of the sheath in the cannula.
(c) Optionally clip the cable tautly to the outer surface of the cannula. (This is recommended if the anchoring procedure is likely to push the lead deeper into the brain.)
(d) Anchor the lead.

(e) Verify lead did not move using test stimulation.
(f) Remove the stylet (if partially retracted).
(g) Remove cable clip attaching the cable to cannula (if the optional step 3 was performed).
(h) Remove the cannula while the immobilized stylet sleeve prevents the lead from retraction.
(i) Remove the stylet sleeve.

Using the above or similar steps, the introduction tools can be disassembled and removed without manually holding the lead at the burr hole exit, or with only minimal manual intervention. A positive constraint on the lead at all times during removal of the tools minimizes inadvertent lead dislodgement. Since the last tool to remove, the stylet sleeve, is only in end-to-end contact with the outer end of the sheath, it's removal does not generate any traction on the lead.

This is in contrast to the presently practiced methods where a brain-entering cannula must be first retracted from the brain and raised above the skull to expose enough lead at the exit from the burr hole so that the lead could be immobilized there (typically by holding the lead manually) and therapy verified, before introduction tool are completely disassembled and removed.

FIGS. 50 and 51 illustrate how the above disclosed leads and introduction tools can be advantageously adapted for use with microelectrode probes. A microelectrode probe has a very small active electrode surface and can identify small cell structures along an insertion trajectory with a high spatial resolution. This allows placement of stimulation leads with a sub-millimeter accuracy thus improving the prospect of optimal therapeutic effect. The process of arriving at the final and efficacious location using microelectrodes and test stimulation is known in the art.

The method described below employs a stereotactic system, a microdrive, and microelectrodes that are available in the art, but seeks to improve the mechanics of the procedure by taking advantage of the novel features of the leads and introduction tools disclosed.

In FIGS. 50-51, a microdrive assembly 220 is rigidly mounted on stop holder 203 (partially shown), which is slidably connected to the stereotactic instrument holder 204 (FIG. 48A). A micrometer-based microdrive is shown but any of the drives used in the art may be employed. The microdrive has a microelectrode holder 221 attached to a carriage 222 which is driven by a lead screw 223. The translation of the carriage is indicated by a micrometer scale at 224. The position of the microelectrode carriage may be referenced to the stationary micrometer frame using a scale 225.

The microelectrode holder has a sleeve 226 with a central opening which slidably receives the microelectrode and also has a means to couple the microelectrode to the microelectrode holder, such as a set screw 227. The sleeve is made from a soft, preferably elastomeric material and acts as a protective interposer between the screw and the microelectrode in order to prevent damage to the microelectrode body. The protective sleeve may have a conductor 228, or a contact, adapted to make an electrical connection to the exposed microelectrode core when screw 227 is clamped. Alternatively, a connector can be attached to an exposed proximal end 229 of the microelectrode.

Handle 230 is a modified version of the handle of FIG. 49A adapted to couple to the microelectrode probe using screw 231 or other coupling means. A soft protective sleeve 232 such as the one in electrode holder can be used to protect the microelectrode from clamping damage. Multiple clamping screws can be used to distribute the clamping pressure uniformly (e.g., three screws 120 degrees apart). Alternatively, the coupling means can be a spring loaded coupling, a collet coupling, or other type of coupling known in the art.

The microelectrode may be pre-inserted into the introduction tools concurrent with the lead or added at any time during the lead introduction procedure. If the microelectrode is pre-inserted in the lead, the distal tip of the microelectrode may be retracted into the distal tip of the lead in order to protect the microelectrode tip. For example the tip of the microelectrode can be flush with the distal tip of the lead, which also establishes a convenient reference for relative displacement. Once the microelectrode is in the lead, the coordinates of the reference position are noted and can be tracked as the microelectrode and/or lead are advanced or retracted.

The microelectrode can be advanced or retracted independently of the lead or in unison with the lead. In order to advance the microelectrode independently, the microelectrode probe is coupled to microelectrode holder 221 and decoupled from handle 230. In order to advance or retract the microelectrode in unison with the lead using the microdrive, the microelectrode is coupled to both the microelectrode holder and the handle. In order to advance the microelectrode in unison with the lead without using the microdrive, the microelectrode is decoupled from the microelectrode holder and coupled to the handle.

After the lead is brought to a desired position above the theoretical target, the microelectrode is advanced, for example to a location 15 mm above the target, and a microelectrode recording is performed. Microelectrode recording is repeated at small steps along the insertion trajectory until a promising stimulation site is identified. The lead is then advanced to the identified site and a test stimulation is performed using the lead, to confirm the stimulation is safe and effective. The microelectrode is decoupled from the microelectrode holder and, if necessary, from handle 230 and removed. The remaining steps of the tools removal can be similar to those described above.

If the sheath has an optional built-in cutting thread such as shown in FIGS. 52 and 53, the retention fit between the stylet and the sheath can be released by pulling on the cutting wire and slitting the retentive portion of the sheath.

In FIG. 52, the retentive portion 240 of the sheath is separate from the portion 36 of the sheath where cable 29 merges tangentially into the sheath wall. A cutting thread 241 emerges from both ends of retentive portion 240 and may be forming a loop 242. The retentive section may be weakened at 243, adjacent to the cutting thread, to facilitate severing of the retentive portion and clean separation of the cutting thread.

In FIG. 53, depicting a lead with a centrally exiting cable (such as lead 130 of FIG. 28) the retentive section of the sheath is independent from the cable since there is no cable within the wall of the sheath. A cutting thread 244 is shown emerging from one end of the cuttable section but a looping configuration of FIG. 52 can be used instead. The retentive section may be weakened at 245, adjacent to the cutting thread, to facilitate a controlled cut and a clean separation of the cutting thread.

In either of the two cable embodiments above, the cuttable sections do not contain the cable so the cable is not affected by the cutting action. The cutting force does not need to be high since the sections involved are thin and may be further weakened by scoring. The peeling or cutting force should preferably be directed radially and somewhat upwardly since the lead is fully constrained in those directions by the stylet means and the cannula. The cutting action will therefore not cause an unintended lead displacement. Cannula 180 can be made adequately rigid to sustain the cutting or peeling force without appreciable deflection since the cannula is completely out of the brain and there is no strict limit on the cannula's outside diameter.

FIGS. 54-55 show an embodiment of a lead with a peelable cable portion 250. Cable portion 250 is adhesively but peelably attached to stylet 251 at 252 and is separated from sheath 253 by slits 254. The adhesive attachment of the cable to the lead provides alternate retention mechanism to maintain the lead on the stylet. The cable is peeled away from the stylet when the lead localization is finalized. The cable can then be immobilized or anchored at the burr hole before the stylet is removed. Use of the stylet sleeve as described in the specification is therefore optional. If a stylet sleeve is not used, the stylet portion 255 is adapted to be slidably guided in the lumen of cannula 180.

FIG. 56 is a cross-sectional view equivalent to that in FIG. 55, but showing yet another cable-to-stylet retention mechanism. Cable portion 260 is retained in a slot 261 of stylet 262 by an interference fit, a friction fit, a peelable adhesive, by mechanical interlocking (such as a protrusion on the cable's body and a complementary groove on the stylet body) or a combination thereof.

Advantages

From the description above, a number of advantages of various embodiments of the disclosed connector will be evident:

(a) A cannula is not inserted into the brain, thus eliminating disruption of brain tissue due to introduction of a cannula.

(b) A slotted cannula allows the lead's conductor cable and the proximal connector to bypass the lead introduction tools. Since the conductor cable and the proximal connector are decoupled from the stylet and the lead introduction tools, each functional part of the lead can be optimized for their functions.

(c) A variety of conductor and cable constructions can be used to provide flexibility and high crush resistance. The conductor cable can have a small diameter and a desirably short length, which are not dictated by lead-introduction tools.

(d) The proximal connector is decoupled from the introduction tools and does not need to be passable through a cannula. The proximal connector terminal can be adapted to mate with any device or test connector available in the art. The connector can remain intra-operatively connected to a device or test unit throughout the entire procedure without interfering with the lead-introduction tools.

(e) The device can be permanently connected to the proximal end of the cable, which reduces the device's size and the cable's length. The smaller components can be co-located in one surgical site, thus minimizing disruption of the cranial tissue.

(f) Only brain-implantable electrode terminal and the sheath receive the stylet and engage the introduction tools. A robust construction of the distal portion of the lead and a short stylet engagement length allow the stylet to be re-inserted once removed.

(g) The introduction tools can be disassembled and removed with minimal direct manual handling of the lead. A stylet sleeve holds the lead from retracting when a cannula or a stylet is being removed.

(h) The disclosed leads and introduction tools are compatible with standard stereotactic instrumentation and localization procedures, including those utilizing microelectrode recording.

(i) The cable peel-away feature allows anchoring the lead at the burr hole while the lead is fully constrained by the introductions tools.

(j) A short interface between the lead and the introduction tools minimizes placement errors by reduced traction-induced forces on the lead when the lead is introduced and when the tools are removed.

(k) The use of inserts to connect wires to electrodes provides robust, small dimensioned electrode terminals which are economical to fabricate.

(l) The externalized stylet sleeve can have graduated marks to index insertion depth. Unlike marks on a lead body, the marks on the stylet sleeve are not subject to stretching.

Further advantages will be evident to those skilled in the art.

RAMIFICATIONS AND SCOPE

The disclosed leads and introduction tools are applicable to a variety of implantable systems having sensing and/or stimulation leads or other similarly shaped components such a catheter.

Lead designs and lead introduction tools disclosed in the context of brain stimulation are also applicable for introducing leads, catheters, or similarly shaped devices into other parts of the body.

While the leads and introduction tools have been described by means of specific embodiments, numerous modifications and variations known to those skilled in the art or disclosed may be employed without departing from the scope of the invention set forth in the claims. For example, the materials, dimensions, shapes, and sizes of all parts may be adapted to a particular need.

All materials referenced in connection with implantable leads, probes, devices, and other implantable accessories are biocompatible and accepted for implantation in the human brain or other living tissue. The term "biocompatible" or "implantable grade" is therefore implicit when these materials are listed.

The leads are shown having four electrodes and four conductors but a single electrode or any number of electrodes can be employed. In any case, the lead will have at least one electrode at the distal end which is electrically connected to at least one contact at the proximal end. Additional electrodes may be used so that the electrode or electrodes providing optimum therapeutic effect could be selected. Redundant electrodes can also be used to adjust the therapy non-invasively, without requiring a corrective surgery, when the therapy through the originally assigned electrodes becomes ineffective, e.g., due to migration of the lead.

The number of conductors typically corresponds to the number of electrodes but may be different depending on the desired connectivity.

The outer surface of the electrodes can be cylindrical, convex or barrel-shaped, spherical, or may have other smooth shape to provide desired stimulation. The electrodes can be segmented, e.g., providing two independent semi-circular electrodes in place of a single ring electrode, so that the stimulation could be activated on one side but turned off on the other side.

The electrode terminal construction and conductor-to-electrode termination methods can be applied to a wide variety of leads such as cardiac pacing leads and electrophysiologic testing leads.

The stylet may be of a multi-piece construction, with two or more pieces joined by welding, press-fit, or slidably assembled together.

The cannula and the cannula guide may be slotted throughout. The cannula or the stylet means may be longitudinally splittable. The stepped lumen may be provided by an adapter mounted at the distal end of the cannula.

The stop can have an anti-rotation feature to align the lead's cable with the slot in the cannula. The stylet can be coupled to the stop and keyed to the stop holder to prevent rotation.

The contact array of the connector terminal can be rectangular, polar, or may have any desired configuration.

Thus the scope should be determined, not by the examples or specifics given, but by the appended claims and their legal equivalents.

I claim:

1. An implantable electrical lead having a proximal end and a distal end, said lead comprising:
   (A) an electrode terminal having a body and at least one electrode at said distal end;
   (B) a connector terminal having a body and at least one contact at said proximal end;
   (C) a tubular sheath extending proximally from said body of said electrode terminal, said sheath having a wall, a proximally facing opening, and an outer end; and
   (D) a conductor cable extending from said outer end of said sheath to said connector terminal; said cable having an insulating body and at least one conductor, said insulating body merging tangentially into said sheath wall; wherein said conductor extends within said sheath wall to said electrode terminal; and wherein said conductor electrically connects said electrode to a respective contact;
   whereby said lead can be introduced into an anatomical target in a human body using a stylet inserted into said sheath opening wherein said stylet bypasses said connector terminal and said cable.

2. The lead of claim 1 wherein said sheath wall is locally thickened to accommodate each said conductor.

3. The lead of claim 1 wherein said cable insulating body is stretchable and has a lumen, and each said conductor is individually insulated and loosely fitted in said lumen, and wherein the axial length of each conductor is greater than the axial length of said cable body, so that no axial tension is applied to said conductor when said cable body is stretched to a length not exceeding the length of said conductor.

4. The lead of claim 1 wherein said cable further comprises an elastomeric core, each conductor being helically wound onto said elastomeric core.

5. The lead of claim 1 wherein each conductor is a stranded conductor having a plurality of conductive strands twisted together.

6. The lead of claim 1 wherein the outside diameter of said electrode terminal is smaller than the outside diameter of said sheath.

7. The lead of claim 1 wherein said sheath and said body of said electrode terminal are made from a material selected from the group consisting of silicone rubber, polyurethane, and silicone-urethane copolymer.

8. The lead of claim 1, further including a stylet, said stylet having a distal portion, a proximal portion, and a body portion, said body portion of said stylet conforming closely to said opening of said sheath.

9. The lead of claim 8, further including a retention mechanism having an attachment selected from the group consisting of an interference fit, a peelable adhesive, a shearable adhesive, a cuttable connection, and any combination thereof, wherein a portion of said sheath adjacent to said outer end is retentively engaged with said body portion of said stylet by said retention mechanism.

10. The lead of claim 9 wherein said retention mechanism is of the type that can be released by pulling on said stylet while holding said sheath immobilized.

11. The lead of claim 9, further comprising a cutting thread in said portion of said sheath adjacent to said outer end, wherein said retention mechanism is of the type that can be released by pulling on said cutting thread while holding said sheath immobilized.

12. The lead of claim 8, further including a retention mechanism having an attachment selected from the group consisting of an interference fit, a peelable adhesive, a shearable adhesive, a mechanical interlock, and any combination thereof, wherein said stylet is retentively engaged with said cable by said retention mechanism, whereby said retention mechanism is of the type that can be released by pulling on said cable while holding said sheath immobilized.

13. The lead of claim 8 wherein said electrode terminal body has a central lumen, and wherein said distal portion of said stylet is slidably accommodated in said lumen.

14. The lead of claim 8, further including a tubular stylet sleeve slidably installed over said stylet, said stylet sleeve having a distal end and a proximal end, said distal end of said stylet sleeve being in end-to-end contact with said outer end of said sheath, whereby said stylet can be removed from said sheath while holding said sheath immobilized with the aid of said stylet sleeve.

15. The lead of claim 14 wherein the outside diameter of said stylet sleeve is substantially equal to the outside diameter of said sheath, whereby both said stylet sleeve and said sheath can be guided continuously in a lumen of a cannula.

16. The lead of claim 14 wherein the outside diameter of said stylet sleeve is greater than the outside diameter of said sheath, whereby said stylet sleeve and said sheath can be guided in respective lumens of a stepped lumen cannula.

17. The lead of claim 14 wherein said stylet further comprises a handle coupled to said proximal portion of said stylet, and wherein said handle is in contact with said proximal end of said stylet sleeve, whereby said stylet sleeve is captivated between said outer end of said sheath and said handle.

18. The lead of claim 14 further comprising a retention mechanism having an attachment selected from the group consisting of an interference fit, a peelable adhesive, a mechanical interlock, and any combination thereof, wherein said stylet is retentively engaged with said cable by said retention mechanism; whereby said retention mechanism can be released by pulling on said cable, away from said stylet means, while holding said stylet and said stylet sleeve immobilized.

19. The lead of claim 14 further comprising a retention mechanism having an attachment selected from the group consisting of an interference fit, a shearable adhesive, a mechanical interlock, and any combination thereof, wherein a portion of said sheath adjacent to said outer end is retentively engaged with said body portion of said stylet by said retention mechanism, whereby said retention mechanism can be released by pulling on said stylet while holding said sheath immobilized by said stylet sleeve is held immobilized.

20. The lead of claim 14 wherein said stylet sleeve has graduation marks on said outer surface.

21. The lead of claim 8 wherein said stylet has a lumen adapted to slidably receive a microelectrode.

22. A lead of claim 8 wherein at least a portion of said stylet body has a slot, and wherein a portion of said cable is retentively accommodated in said slot, whereby said cable can be disengaged from said slot by pulling on said cable while holding said sheath immobilized.

23. The lead of claim 8, wherein said body portion of said stylet and said opening of said sheath are substantially circular, said body portion of said stylet having an outside diameter sized for a close fit in said opening of said sheath.

24. The lead of claim 8, wherein said body portion of said stylet and said opening of said sheath are substantially D-shaped.

25. The lead of claim 1 wherein said anatomical target is within the brain.

26. The lead of claim 1 wherein said electrode terminal further comprises a reinforcing tube.

27. The lead of claim 26 further comprising a stylet having a distal portion, said distal portion having a counterbore; wherein said reinforcing tube extends from said body of said electrode terminal into said opening of said sheath; and wherein said counterbore slidably accommodates said reinforcing tube.

28. The lead of claim 26 wherein said reinforcing tube material is selected from the group consisting of platinum, platinum-iridium, stainless steel, titanium, and titanium alloy.

29. The lead of claim 26, further comprising a conductive tip, said tip joined to said reinforcing tube.

30. The lead of claim 1 wherein said connector terminal body is paddle shaped and said contacts are disposed in a planar array.

31. The lead of claim 1, further comprising a conductive tip, said tip forming a tip electrode, said tip electrode electrically connected to said conductor of said cable.

32. The lead of claim 1, further comprising a conductive insert attached to said electrode, said conductor being joined and electrically connected to said insert, and said insert being joined and electrically connected to said electrode.

33. The lead of claim 32 wherein said insert is arcuate and has an outer surface, and wherein said electrode further has a cross-hole and an inner surface, said cross-hole having an edge, said inner surface of said electrode locating said outer surface of said insert, said outer surface of said insert being joined to said edge of said cross-hole.

34. The lead of claim 32 wherein said insert is arcuate and has an outer surface, and wherein said electrode has an inner surface and a rim, said inner surface locating said outer surface of said insert, said outer surface of said insert being joined to said rim of said electrode.

35. The lead of claim 32 wherein said insert has an outer surface and an edge, and said electrode has a cutout, said cutout having an edge that is complementary to said edge of said insert, said perimeter edge of said insert being joined to said complimentary edge of said cutout of said electrode.

36. The lead of claim 32 wherein said insert is button shaped and has a substantially round weld side, and wherein said electrode further has a cross-hole adapted to accommodate said substantially round weld side of said insert, said insert being joined to said electrode at complementary edges of said weld side and said cross-hole.

37. The lead of claim 32 wherein said insert is tubular and has a body portion, and wherein said electrode further has an arcuate cutout and a cross-hole, said cross-hole having an edge, said arcuate cutout locating said body of said tubular insert, said body of said insert being joined to said edge of said cross-hole.

38. The lead of claim 1 wherein said electrode terminal and said sheath have a predetermined combined length greater than the depth of a predetermined anatomical targets in a human body.

39. The lead of claim 1 wherein said cable comprises a plurality of said conductors, each conductor being pre-insulated and embedded in said cable insulating body, and wherein at least a portion of said cable has a wavy form.

40. The lead of claim 39, further comprising a stretchable tubular cable casing, and at least a portion of said cable being encased in said cable casing.

41. The lead of claim 39 wherein said wavy form is imparted to said cable insulating body by heat forming.

42. The lead of claim 39 wherein said conductors are arranged side-by-side in a ribbon configuration.

43. The lead of claim 1, further including a device electrically connected to said connector terminal, said device being selected from the group consisting of a test stimulation device, a sensing device, a recording device, an implantable device with a separable connection to said lead, and an implantable device with a non-separable connection to said lead, whereby said device does not interfere with lead introduction tools.

44. A lead introduction system for introducing an implantable electrical lead into an anatomical target in a human brain, said lead introduction system comprising:

(A) an implantable electrical lead comprising a tubular distal portion having an opening, a wall, and an outer end; said distal portion comprising an electrode terminal with at least one electrode; the lead further comprising a proximal connector terminal having at least one contact; and a conductor cable comprising at least one conductor connecting said electrode to said contact; said cable merging into said wall of said tubular distal portion;

(B) a stylet means comprising a stylet and a stylet sleeve, said stylet means cooperating with said distal portion of said lead while bypassing said connector and at least a portion of said conductor cable; said stylet slidably assembled in said stylet sleeve and slidably received in said opening of said distal portion of said lead; said stylet sleeve having a distal end, a proximal end, and an outer surface, wherein said distal end of said stylet sleeve is in end-to-end contact with said outer end of said distal portion of said lead;

(C) a retention mechanism wherein said stylet means is retentively engaged with said lead, whereby said retention mechanism enables said distal portion of said lead to advance and retract in unison with said stylet means when said lead is being introduced into said anatomical target;

(D) a cannula having a proximal end, a distal end, a lumen, and a lengthwise slot; said lumen adapted to slidably guide said stylet sleeve; said slot originating at said distal end of said cannula and forming a side opening contiguous with said lumen; said side opening having a predetermined length sufficient to allow said distal portion of said lead to be fully inserted into said cannula lumen from said distal end of said cannula; whereby said side opening of said cannula provides a passage for said cable when said lead is advanced along said lumen of said cannula, thereby allowing said connector terminal and at least a portion of said cable to bypass said cannula;

(E) a stereotactic frame comprising a cannula guide holder and a stop holder which are rigidly and adjustably attached to said stereotactic frame;

(F) a cannula guide adapted to be retained in said cannula guide holder, said cannula guide having an opening adapted to slidably receive and retain said cannula; and (G) a stop bushing adapted to be retained in said stop holder; said stop bushing having a lumen adapted to slidably guide said stylet sleeve; said stop bushing adapted to couple said stylet sleeve to said stop bushing, so that:
  (1) when said stylet sleeve is uncoupled from said stop bushing, said lead can be slidably advanced or refracted through said lumen of said stop bushing;
  (2) when said stylet sleeve is coupled to said stop bushing, said lead can be advanced, retracted, or immobilized in unison with said stop holder; and
  (3) when said stylet sleeve is immobilized in said stop bushing, said stylet can by pulled out of said distal portion of said lead without causing said lead to retract.

45. A lead introduction system of claim 44 wherein said retention mechanism has an attachment selected from the group consisting of an interference fit, a peelable adhesive, a mechanical interlock, and any combination thereof, wherein said retention mechanism is of the type that can be released by pulling on said cable, away from said stylet means.

46. A lead introduction system of claim 44 wherein said retention mechanism has an attachment selected from the group consisting of an interference fit, a shearable adhesive, a mechanical interlock, and any combination thereof, whereby said retention mechanism is of the type that can be released by pulling on said stylet while said distal portion of said lead is immobilized by said stylet sleeve.

47. The lead introduction system of claim 44 wherein said stylet means further comprises a handle coupled to said stylet, said handle being in contact with said proximal end of said stylet sleeve, said stylet sleeve being captivated between said outer end of said distal portion of said lead and said handle, whereby said handle will cooperate with said stop bushing to provide a pre-determined initial desired location of said electrode terminal along the lead insertion trajectory defined by said cannula.

48. The lead introduction system of claim 47 wherein said stylet has a lumen adapted to slidably guide a microelectrode probe, and said stereotactic frame has a microdrive rigidly attached to said stop holder, and wherein said microdrive has a carriage having a microelectrode holder; said microelectrode holder adapted to couple said microelectrode to said carriage so that said microelectrode can be advanced and refracted in fine increments using said microdrive.

49. The lead introduction system of claim 48 wherein said handle is further adapted to couple said microelectrode, so that:
  (1) when said microelectrode is coupled to said carriage and decoupled from said handle, said microelectrode can be advanced or retracted independently of said lead;
  (2) when said microelectrode and said stylet are coupled to said handle and said microelectrode is coupled to said carriage, said microelectrode and said lead can be advanced or retracted in unison using said microdrive; and
  (3) when said microelectrode is decoupled from said carriage and coupled to said handle; said microelectrode can be advanced or retracted in unison with said lead without using said microdrive.

50. The lead introduction system of claim 48 wherein said microelectrode has a tubular metal casing which enables said microelectrode to serve as a stylet.

51. The lead introduction system of claim 44, further including an implantable device electrically connected to said connector terminal of said lead, whereby said device can remain connected during entire lead introduction procedure without interfering with the lead introduction tools.

52. The lead introduction system of claim 44 wherein said stylet sleeve has graduation marks on said outer surface.

53. A lead introduction system for introducing an electrical lead into an anatomical target in a human body, said lead comprising a tubular distal portion having an opening, a wall, and an outer end; said distal portion comprising an electrode terminal with at least one electrode; said lead further comprising a proximal connector terminal having at least one contact, and a conductor cable comprising at least one conductor connecting said electrode to said contact, said cable merging into said wall of said tubular distal portion;
  said lead introduction system comprising:
    (A) a stylet means comprising a stylet and a stylet sleeve, said stylet means cooperating with said distal portion of said lead while bypassing said connector terminal and at least a portion of said conductor cable; said stylet slidably assembled in said stylet sleeve and slidably received in said opening of said distal portion of said lead; said stylet sleeve having a distal end, wherein said distal end of said stylet sleeve is in end-to-end contact with said outer end of said distal portion of said lead;
    (B) a retention mechanism wherein said stylet means is retentively engaged with said lead, whereby said retention mechanism enables said electrode terminal to advance and retract in unison with said stylet means when said lead is being introduced into said anatomical target; and
    (C) a cannula having a distal end, a lumen, and a lengthwise slot, said lumen adapted to slidably guide said stylet sleeve; said slot originating at said distal end of said cannula and forming a side opening contiguous with said lumen, said side opening having a predetermined length sufficient to allow said distal portion of said lead to be fully inserted into said cannula lumen from said distal end of said cannula;
  whereby said side opening of said cannula provides a passage for said cable when said lead is advanced along said lumen of said cannula, thereby allowing said connector terminal and at least a portion of said cable to bypass said cannula.

54. The lead introduction system of claim 53 further comprising:
  (D) a stereotactic frame
  (E) a cannula guide holder rigidly and adjustably attached to said stereotactic frame; and
  (F) a cannula guide adapted to be retained in said cannula guide holder, said cannula guide having and opening adapted to slidably receive and retain said cannula.

55. The lead introduction system of claim 54 further comprising:
  (G) a stop holder which is rigidly and adjustably attached to said stereotactic frame;
  (H) a stop bushing adapted to be retained in said stop holder; said stop bushing having a lumen adapted to slidably guide said stylet sleeve; said stop bushing adapted to couple said stylet sleeve to said stop bushing, so that:
    (1) when said stylet sleeve is uncoupled from said stop bushing, said lead can be slidably advanced or retracted through said lumen of said stop bushing;
    (2) when said stylet sleeve is coupled to said stop bushing, said lead can be advanced, retracted, or immobilized in unison with said stop holder; and
    (3) when said stylet sleeve is immobilized in said stop bushing, the stylet can pulled out of the lead without causing said lead to retract.

56. The lead introduction system of claim 55 further comprising a handle coupled to said stylet means, said handle being arranged to cooperate with said stop bushing to provide a pre-determined initial desired location of said electrode terminal along the lead insertion trajectory defined by said cannula.

57. A lead introduction system of claim 53 wherein said retention mechanism has an attachment selected from the group consisting of an interference fit, a peelable adhesive, a mechanical interlock, and any combination thereof, wherein said retention mechanism is of the type that can be released by pulling on said cable, away from said stylet means.

58. A lead introduction system of claim 53 wherein said retention mechanism has an attachment selected from the group consisting of an interference fit, a shearable adhesive, a mechanical interlock, and any combination thereof, whereby said retention mechanism is of the type that can be released by pulling on said stylet while said distal portion of said lead is immobilized by said stylet sleeve.

59. An implantable electrical lead having a proximal end and a distal end, said lead comprising:
   (A) an electrode terminal having a body and at least one electrode at said distal end;
   (B) a connector terminal having a body and at least one contact at said proximal end;
   (C) a centrally disposed conductor cable extending from said electrode terminal to said connector terminal; said cable having an insulating body and at least one conductor; said conductor electrically connecting said electrode to a respective contact; and
   (D) a tubular sheath extending proximally from said body of said electrode terminal, said sheath having a wall and an outer end; said wall concentrically enclosing a portion of said cable adjacent to said electrode terminal; said wall being spaced from said cable to form a proximally facing annular opening; whereby said lead can be introduced into an anatomical target in a human body using a stylet inserted into said annular opening; wherein said stylet has a side opening which enables the stylet to bypass said connector and a substantial portion of said cable.

60. The lead of claim 59 wherein the outside diameter of said electrode terminal is smaller than the outside diameter of said sheath.

61. The lead of claim 59 wherein said electrode terminal further comprises a stiffening tube; wherein said at least one conductor of said cable extends within said stiffening tube toward said electrode, said stiffening tube having a lengthwise slot, wherein said slot provides a passage for each conductor that is connecting to a respective electrode.

62. The lead of claim 61 further comprising a stylet having a distal portion, said distal portion being substantially arcuate; wherein said stiffening tube extends from said body of said electrode terminal into said opening of said sheath; and wherein said arcuate distal portion of said stylet slidably accommodates said stiffening tube.

* * * * *